United States Patent [19]

Bajusz et al.

[11] Patent Number: 5,760,235
[45] Date of Patent: Jun. 2, 1998

[54] ANTICOAGULANT PEPTIDE DERIVATIVES AND PHARMACEUTICAL COMPOSITIONS CONTAINING THE SAME AS WELL AS A PROCESS FOR PREPARATION THEREOF

[75] Inventors: Sándor Bajusz; Dániel Bagdy; Éva Barabás; András Fehér; Gabriella Szabó; Györgyné Széll; Bélané Véghelyi; Gyula Horváth; Attila Juhász; Jánosné Lávich; Lászlóné Mohai; Imre Moravcsik; Gáborné Szeker; István Pallagi; Katalin Pálné Aranyosi, all of Budapest, Hungary

[73] Assignee: Gyogyszerkutato Intezet Kft., Budapest, Hungary

[21] Appl. No.: 740,009

[22] PCT Filed: Mar. 4, 1993

[86] PCT No.: PCT/HU93/00013

§ 371 Date: Dec. 5, 1994

§ 102(e) Date: Dec. 5, 1994

[87] PCT Pub. No.: WO93/18060

PCT Pub. Date: Sep. 16, 1993

Related U.S. Application Data

[63] Continuation of Ser. No. 302,724, Dec. 5, 1994, abandoned.

[30] Foreign Application Priority Data

Mar. 4, 1992 [HU] Hungary .................. P 92 00725
May 19, 1992 [HU] Hungary .................. P9201657

[51] Int. Cl.$^6$ .............. A61K 38/05; C07K 5/078
[52] U.S. Cl. .............. 546/226; 514/20; 546/193; 546/196; 546/205; 548/518; 548/524; 548/525; 548/537

[58] Field of Search .............. 514/19, 20; 546/262, 546/323, 282.7, 226, 193, 196, 205; 548/518, 524, 525, 537

[56] References Cited

U.S. PATENT DOCUMENTS

| | | | |
|---|---|---|---|
| 4,316,889 | 2/1982 | Bajusz et al. | 514/19 |
| 4,703,036 | 10/1987 | Bajusz et al. | 530/331 |
| 5,380,713 | 1/1995 | Balasubramanian et al. | 514/18 |
| 5,416,093 | 5/1995 | Shuman | 514/307 |
| 5,430,023 | 7/1995 | Gesellchen et al. | 514/18 |

FOREIGN PATENT DOCUMENTS 479489  4/1992  European Pat. Off. .

OTHER PUBLICATIONS

Copy of U.S. Patent Application Serial No. 07/756,091, filed Sep. 6, 1991, Which is the Parent to U.S. 5,430,023.

*Primary Examiner*—Jeffrey E. Russel
*Attorney, Agent, or Firm*—Keil & Weinkauf

[57] ABSTRACT

This invention relates to new peptide derivatives of the general formula (I) A-Xaa-Arg-H, wherein A represents a D- or L-isochroman-1-carbonyl, D- or L-isochroman-3-carbonyl group, furthermore an acyl group of the general formula: D- or DL-A'—CH(OH)—CO, wherein A' represents a phenyl, benzyl, 1-naphthyl, 1-naphthylmethyl, 2-naphthyl, 2-naphthylmethyl, 9-fluorenyl, benzhydryl, cyclohexyl, cyclohexylmethyl, 2-pyridyl, 3-pyridyl or 4-pyridyl group, and Xaa represents an L-prolyl or an L-pipecolinic acid residue, and Arg stands for an L-arginine residue, their acid addition salts formed with an organic or inorganic acid and pharmaceutical compositions containing the same. Furthermore the invention relates to a process for preparing them. The compounds of the invention have valuable therapeutic, particularly anticoagulant, properties.

3 Claims, No Drawings

5,760,235

ANTICOAGULANT PEPTIDE DERIVATIVES AND PHARMACEUTICAL COMPOSITIONS CONTAINING THE SAME AS WELL AS A PROCESS FOR PREPARATION THEREOF

This application is a continuation of application Ser. No. 08/302,724, filed on Dec. 5, 1994 now abandoned.

This invention relates to new peptide derivatives of the general formula (I),

A-Xaa-Arg-H    (I)

wherein

A represents a D- or L-isochroman-1-carbonyl, D- or L-isochroman-3-carbonyl group, furthermore an acyl group of the general formula D- or DL-A'—CH(OH)—CO, wherein A' represents a phenyl, benzyl, 1-naphthyl, 1-naphthylmethyl, 2-naphthyl, 2-naphthylmethyl, 9-fluorenyl, benzhydryl, cyclohexyl, cyclohexylmethyl, 2-pyridyl, 3-pyridyl or 4-pyridyl group, and Xaa represents an L-prolyl or an L-pipecolinic acid residue, and Arg stands for an L-arginine residue, their acid addition salts formed with an organic or inorganic acid and pharmaceutical compositions containing the same. [The abbreviation of the L-arginine residue as Arg is in accordance with the prior art, e.g. Biochem. J. 126, 773 (1972); Biochemistry 14, 449 (1975)].

The invention furthermore relates to a process for preparing the new peptide derivatives of the general formula (I) and pharmaceutical compositions containing these compounds.

The compounds of the invention have valuable therapeutic, particularly anticoagulant properties.

Preferred representatives of the compounds having the formula (I) are those described in the Examples.

Particularly preferred representatives of the compounds according to the invention are the following derivatives:

3-cyclohexyl-D-lactyl-L-prolyl-L-arginine aldehyde hemisulfate;

3,3-diphenyl-D-lactyl-L-prolyl-L-arginine aldehyde hemisulfate;

D-2-cyclohexyl-2-hydroxyacetyl-L-prolyl-L-arginine aldehyde hemisulfate;

D-2-(1-naphthyl)-2-hydroxyacetyl-L-prolyl-L-arginine aldehyde hemisulfate;

D-2-(2-naphthyl)-2-hydroxyacetyl-L-prolyl-L-arginine aldehyde hemisulfate.

It is known that the aldehyde, derived from the tripeptide D-phenylalanyl-L-prolyl-L-arginine (Hungarian patent specification No. 169,870 and U.S. Pat. No. 4,399,065), the trifluoromethyl-ketone [Neises and Tarnus: Thrombos Haemostas 65, 1290 (1991)], and the boro-arginine [Kettner et al.: J. Biol. Chem. 265, 18289 (1990)] are potent anticoagulants exerting activity both in vitro and in vivo. However, these compounds are rather unstable and are converted in neutral aqueous solution to inactive products [Bajusz et al.: J. Med. Chem. 33, 1729 (1990)].

Further active tripeptide derivatives were prepared by acylating [U.S. Pat. No. 4,478,475 and Kettner et al.: J. Biol. Chem. 265, 18289 (1990)) or alkylating (U.S. Pat. No. 4,703,036) the D-phenylalanine moiety, or by exchanging it for analogue amino or imino acids such as N-methylphenylglycine or 1,2,3,4-tetrahydroisoquinoline-1-carboxylic acid [Shuman et al.: Peptides, Proceedings of the Twelfth American Peptide Symposium (Eds. J. A. Smith and J. E. Rivier), ESCOM, Leyden, pp. 801–802, 1992]. It is a characteristic feature of highly active anticoagulant peptides that they are tripeptide derivatives, and the N-terminal residue, linked to the central L-proline moiety, is an amino or imino acid residue. These tripeptides correspond to the general formula (I) only if A stands for a D-phenylalanine residue, and acylated or alkylated derivative an amino acid or imino acid analogue thereof.

It is the objective of the present invention to provide novel peptide derivatives of improved stability and bioavailability compared to known compounds.

It was unexpectedly found that the tripeptide structure is not a prerequisite of anticoagulant activity, a carboxylic acid group containing an oxygen atom in the alpha-position [A in general formula (I)] can be advantageously substituted for the N-terminal amino acid or imino acid moiety of the known compounds.

Furthermore it has also been found that the compounds of the general formula (I) according to the invention, wherein A, A', Xaa and Arg have the same meaning as above, and their acid-addition salts are stable in aqueous solution, exert strong anticoagulant activity both in vitro and in vivo, and have favorable bioavailability.

According to the invention the compounds of general formula (I) and their acid-addition salts formed with an organic or inorganic acid are prepared by a process which comprises condensing an acid, containing an acyl radical A, wherein A has the above meaning, and L-proline or L-pipecolinic acid, converting the thus-obtained acyl-L-proline or acyl-L-pipecolinic acid by a method known in the art by acylating an arginine lactam protected at the guanidino group with the said acyl-L-proline or acyl-L-pipecolinic acid, reducing the protected acyl-arginine lactam to the protected acyl-arginine aldehyde and removing the protecting groups, and, if desired, finally converting the resulting compound of the general formula (I) with an inorganic or organic acid to an acid-addition salt.

Compounds of the general formula (I), wherein A, A', Xaa and Arg have the same meaning as in the introduction, are prepared from the new acyl-L-proline or acyl-L-pipecolinic acid synthesized by the first step of the process of the invention, according to the method as described in the U.S. Pat. No. 4,703,036 disclosing compounds of similar structure.

According to a preferred embodiment of the process according to the invention DL-isochroman-1-carboxylic acid is condensed with L-proline t-butyl ester, the ester group is removed by acidolysis from the DL-acyl-L-proline t-butyl ester formed, then the product is submitted to silica gel column chromatography to separate D- and L-isochroman-1-carbonyl-L-prolin, subsequently D-isochroman-1-carbonyl-L-proline is condensed with $N^G$-benzyloxycarbonyl-L-arginine lactam, the thus-obtained D-iso-chroman-1-carbonyl-L-prolyl-$N^G$-benzyloxycarbonyl-L-arginine lactam is reduced with lithium aluminium hydride to the respective aldehyde, the $N^G$ protecting group is removed by hydrogenolysis in aqueous ethanol solution containing sulfuric acid in the presence of a Pd—C catalyst, the catalyst is filtered off and the product is separated by freeze-drying.

According to an other preferred embodiment of the present invention D-mandelic acid methyl ester is reacted with dihydropyran, the O-tetrahydropyranyl-D-2-phenyl-2-

-hydroxyacetic acid methyl ester formed is saponified, then condensed with L-proline methyl ester, the resulting O-tetrahydropyranyl-D-2-phenyl-2-hydroxyacetyl-L-proline methyl ester is saponified, thereafter condensed with $N^G$-benzyloxycarbonyl-L-arginine lactam and the obtained O-tetrahydropyranyl-D-2-phenyl-2-hydroxyacetyl-L-prolyl-$N^G$-benzyloxycarbonyl-L-arginine lactam is reduced with lithium aluminium hydride to the respective aldehyde, the protecting groups are removed by dissolving the product in aqueous ethanol containing sulfuric acid and by submitting this solution to catalytic hydrogenation in the presence of Pd—C, filtering off the catalyst and isolating the product by freeze-drying.

According to a further preferred embodiment of the present invention DL-2-(2-naphthyl)-2-hydroxyacetic acid methyl ester is converted with isobutene to O-t-butyl-DL-2-(2-naphthyl)-2-hydroxyacetic acid methyl ester, then saponified, the O-t-butyl-DL-2-(2-naphthyl)-2-hydroxyacetic acid obtained is condensed with L-proline methyl ester, the resulting diastereomer pair of O-t-butyl-D-2-(2-naphthyl)-2-hydroxyacetyl-L-proline methyl ester and O-t-butyl-L-2-(2-naphthyl)-2-hydroxyacetyl-L-proline methyl ester is saponified, separated on an anion-exchange resin (acetate cycle), the O-t-butyl-D-2-(2-naphthyl)-2-hydroxyacetyl-L-proline obtained as first product when eluting the column is condensed with $N^G$-benzyloxycarbonyl-L-arginine lactam, the obtained O-t-butyl-D-2-(2-naphthyl)-2-hydroxyacetyl-L-prolyl-$N^G$-benzyloxycarbonyl-L-arginine lactam, after acidic deblocking of the t-butyl group, is reduced with lithium aluminium hydride to the respective aldehyde, the $N^G$-protecting group is removed in aqueous ethanol solution containing sulfuric acid by catalytic hydrogenation in the presence of Pd—C, the catalyst is filtered off and the product is isolated by freeze-drying.

According to a further preferred embodiment of the present invention compounds of the general formula (I), wherein Xaa stands for an L-pipecolic acid residue, are prepared by condensing acyl-L-pipecolic acid and $N^G$-benzyloxycarbonyl-L-arginine lactam in pyridine in the presence of phosphorus oxychloride, the acyl-L-pipecolyl-$N^G$-benzyloxycarbonyl-L-arginine lactam obtained is reduced to the corresponding aldehyde, then after deblocking the last protecting group the product is isolated by freeze-drying.

In the acid-addition salts of the peptide derivatives of general formula (I) the activity resides in the base and the acid is of less importance although for therapeutic purposes it is preferable to use pharmacologically and pharmaceutically acceptable acid-addition salts. Examples of such suitable acids include (a) mineral acids: hydrochloric, hydrobromic, phosphoric, metaphosphoric and sulphuric acids, (b) organic acids: tartaric, acetic, citric, malic, lactic, fumaric, benzoic, glycolic, gluconic, succinic, pamoic and aryl sulphonic acids, for example p-toluenesulphonic acid.

The antithrombin activity of the compounds of general formula (I) was determined by the usual method [Bagdy et al.: Thromb Haemostas 67, 325–330 (1992)] by measuring whole blood clotting time (WBCT), thrombin time (TT) and activated partial thromboplastin time (APTT). The in vitro activity of some compounds of the invention assayed on native human blood (non-anticoagulated clotting) (WBCT) and on citrated blood plasma (TT and APTT) is presented in Table 1.

TABLE 1

In vitro antithrombin effect of new peptide derivatives of general formula (I)

A-Xaa-Arg-H[1]

| Example No. | A | Xaa | Clotting parameters[2] WBCT | TT | APTT |
|---|---|---|---|---|---|
| 1 | D-Ica (1) | Pro | 1.55 | 0.132 | 0.60 |
| 6 | D-Man | Pro | 0.45 | 0.040 | 0.15 |
| 7 | D-Hpl | Pro | 0.32 | 0.072 | 0.20 |
| 8 | D-Hma | Pro | 0.72 | 0.100 | 0.35 |
| 12 | D-Dpl | Pro | 0.52 | 0.077 | 0.12 |
| 13 | D-Nga (1) | Pro | 1.13 | 0.100 | 1.00 |
| 14 | D-Nga (2) | Pro | 1.04 | 0.150 | 0.52 |

[1] Abbreviations: Dpl = 3,3-diphenyl-lactyl, Hma = cyclohexyl-2-hydroxyacetyl, Hpl = 3-cyclohexyl-lactyl, Ica (1) = isochroman-1-carbonyl, Man = 2-phenyl-2-hydroxyacetyl, Nga (1) = 2-(1-naphthyl)-2-hydroxyacetyl, Nga (2) = 2-(2-naphthyl)-2-hydroxyacetyl, Pro = L-prolyl.
[2] WBCT = whole blood clotting time, TT = thrombin time, APTT = activated partial thromboplastin time parameter. The figures represent concentrations of the compounds required to double the clotting time of native whole human blood or of citrated blood plasma.

The in vivo antithrombin effect of the compounds of general formula (I) was treated in rabbits by a known method [Bagdy et al: Thromb Haemost 67, 357–365 (1992)]. The compounds were applied in a dose of 0.5–3.0 mg/kg s.c. and 5–15 mg/kg p.o. The effect was already detectable 15–30 minutes after drug administration, peak effect was attained after 90–120 minutes but the therapeutic effect was dose dependently maintained during 3 to longer than 5 hours.

The in vivo antithrombin effect of 3-cyclohexyl-D-lactyl-L-prolyl-L-arginine aldehyde hemisulfate (Example 7.) is presented in detail in Tables 2 and 3. The compound was administered in doses of 10 and 15 mg/kg, resp., p.o. and the blood samples taken from the ear-vein of the animals were assayed in every 30 minutes. The whole blood clotting time (WBCT) and the inhibition of whole blood platelet aggregation induced by thrombin (IWBA) were determined. Furthermore the citrated plasma thrombin time (TT) of the blood sample and the activated partial thromboplastin time (APTT) were measured, too. The WBCT and APTT values are presented in Table 2 and the TT and IWBA values in Table 3.

TABLE 2

Antithrombin effect of 10 and 15 mg/kg p.o. doses of 3-cyclohexyl-D-lactyl-L-prolyl-L-arginine aldehyde hemisulfate in rabbits. WBCT and APTT values

| Time (min.) | 10 mg/kg | | 15 mg/kg | |
|---|---|---|---|---|
| | WBCT (min.) | APTT (sec) | WBCT (min.) | APTT (sec) |
| 0 | 13.2 ± 1.1 | 27.7 ± 1.2 | 14.6 ± 0.4 | 32.6 ± 4.6 |
| 30 | 17.7 ± 1.6 | 58.9 ± 9.0 | 24.2 ± 4.7 | 115.0 ± 36.6 |
| 60 | 23.6 ± 1.9 | 77.6 ± 14.6 | 29.4 ± 4.5 | 150.4 ± 30.9 |
| 90 | 21.2 ± 2.9 | 65.1 ± 8.4 | 33.0 ± 5.9 | 170.3 ± 18.5 |
| 120 | 18.8 ± 1.0 | 55.1 ± 11.4 | 34.4 ± 4.4 | 145.6 ± 22.7 |
| 150 | 19.2 ± 1.1 | 52.1 ± 6.6 | 27.2 ± 3.6 | 149.2 ± 22.0 |
| 180 | 18.4 ± 1.5 | 53.8 ± 8.5 | 29.5 ± 2.7 | 169.0 ± 23.0 |
| 210 | 17.2 ± 2.3 | 48.6 ± 3.8 | 34.0 ± 5.9 | 137.7 ± 25.8 |
| 240 | 15.8 ± 1.7 | 47.7 ± 7.4 | 33.7 ± 6.5 | 127.4 ± 25.7 |
| 270 | 16.2 ± 2.1 | 44.4 ± 3.7 | 26.0 ± 1.2 | 133.4 ± 24.7 |
| 300 | 13.5 ± 0.9 | 43.7 ± 5.0 | 23.6 ± 3.3 | 92.8 ± 18.4 |

TABLE 3

Antithrombin effect of 10 and 15 mg/kg p.o. doses of 3-cyclohexyl-D-lactyl-L-prolyl-L-arginine aldehyde hemisulfate in rabbits. TT and IWBA values

| Time (min.) | 10 mg/kg | | 15 mg/kg | |
|---|---|---|---|---|
| | TT (sec) | IWBA (%) | TT (sec) | IWBA (%) |
| 0 | 18.4 ± 2.1 | | 18.9 ± 2.1 | |
| 30 | 317.1 ± 123.0 | 89.4 ± 7.6 | 371.2 ± 142.3 | 81.4 ± 11.7 |
| 60 | 416.0 ± 107.2 | 95.8 ± 6.9 | 528.3 ± 72.9 | 97.4 ± 2.6 |
| 90 | 444.7 ± 108.6 | 81.6 ± 8.2 | 578.8 ± 21.5 | 100.0 ± 0 |
| 120 | 264.6 ± 101.3 | 94.0 ± 3.2 | >600.0 ± 0 | 100.0 ± 0 |
| 150 | 201.1 ± 109.9 | 71.4 ± 13.8 | 549.6 ± 34.0 | 100.0 ± 0 |
| 180 | 182.7 ± 113.6 | 72.4 ± 19.2 | 380.7 ± 116.0 | 100.0 ± 0 |
| 210 | 123.0 ± 65.3 | 54.4 ± 21.0 | 342.1 ± 121.2 | 93.7 ± 4.9 |
| 240 | 141.5 ± 81.3 | 50.6 ± 17.7 | 340.9 ± 137.0 | 82.6 ± 17.7 |
| 270 | 65.4 ± 25.7 | 35.2 ± 17.3 | 376.4 ± 153.0 | 81.0 ± 16.9 |
| 300 | 41.8 ± 11.4 | 48.2 ± 16.9 | 261.0 ± 140.8 | 69.6 ± 20.4 |

The compounds of the general formula (I) inhibit clot formation without interfering with the natural lysis of blood clots in the body, e.g. fibrinolysis. This was confirmed by the fact that the compounds of Examples 6, 7 and 8 had only negligible inhibitory effect on fibrinolysis induced by tissue plasminogen activator measured in a thromboelastogram [H. Hartert. Thromboelastography. In: Bang N. U., F. K. Beller, E. Deutsch, E. F. Mammen eds. Thrombosis and Bleeding Disorders. Theory and Methods. Academic Press, London, 1971: 70–76].

The invention in one of its aspects provides a method for inhibiting the formation of blood clots in man and animals which comprises administering to said man or animal an effective clot inhibiting non-toxic dose of a compound represented by the formula (I). The anticoagulant compound is administered orally, parenterally, e.g. by intravenous infusion (i.v.), intramuscular injection (i.m.) or subcutaneously (s.c.). Preferably administration is carried out by subcutaneous injection or orally.

An effective clot inhibiting dose is 0.3 to 3.0 mg/kg, preferably 0.5 to 1.0 mg/kg s.c. and 3 to 20 mg/kg, preferably 5 to 15 mg/kg p.o. The dose regime may vary according to the age and state of the patient, e.g. for prophylactic use a single daily dose may be administered or multiple doses such as 3 or 5 times daily may be appropriate.

The method of this invention is practiced in conjunction with a clot lyzing agent, e.g. tissue plasminogen activator (tPA), modified tPA, streptokinase or urokinase. In cases when clot formation has occurred and an artery or vein is blocked partially or totally, a clot lyzing agent is usually employed. A compound of the invention can be administered along with the lyzing agent or subsequent to its use to prevent the reoccurrence of clot formation.

In carrying out the method the use of a preferred compound of the invention is desirable. For example use is made of a preferred compound such as described hereinabove. Preferred peptide derivatives are 3-cyclohexyl-D-lactyl-L-prolyl-L-arginine aldehyde hemisulfate, 3,3-diphenyl-D-lactyl-L-prolyl-L-arginine aldehyde hemisulfate and D-2-cyclohexyl-2-hydroxyacetyl-L-prolyl-L-arginine aldehyde hemisulfate.

The invention also provides pharmaceutical formulations for use in the above-described therapeutic method. Pharmaceutical formulations of the invention comprise an effective clot inhibitory amount of a compound of the formula (I) or of a pharmaceutically acceptable salt thereof and a pharmaceutically acceptable carrier. For oral administration the antithrombotic compound is formulated in gelatine capsules or tablets which may contain excipients such as binders, lubricants, disintegration agents and the like. For parenteral administration the antithrombotic compound is formulated in a pharmaceutically acceptable diluent, e.g. physiological saline (0.9%), 5% dextrose, Ringer's solution and the like.

The following examples are illustrating but not limiting the scope of the invention.

The $R_f$ values recorded in the examples were determined by thin-layer chromatography, using silica gel as adsorbent (DC-Alufolien Kieselgel 60 $F_{254}$, Merck, Darmstadt) in the following developing solvents:

1. Ethyl acetate-pyridine-acetic acid-water (480:20:6:11)
2. Ethyl acetate-pyridine-acetic acid-water (240:20:6:11)
3. Ethyl acetate-pyridine-acetic acid-water (120:20:6:11)
4. Ethyl acetate-pyridine-acetic acid-water (60:20:6:11)
5. Ethyl acetate-pyridine-acetic acid-water (45:20:6:11)
6. Ethyl acetate-pyridine-acetic acid-water (30:20:6:11)
7. Ethyl acetate-pyridine-formic acid-water (480:20:6:5.5)
8. Ethyl acetate-pyridine-formic acid-water (240:20:6:5.5)
9. Ethyl acetate-pyridine-acetic acid-water (960:20:6:11)
10. Ethyl acetate-diisopropyl ether (7:3)
11. Ethyl acetate-n-hexane (1:1)
12. Chloroform-acetone (98:2).

The capacity factors specified in the examples were determined with the apparatus "Pharmacia LKB analytical HPLC System Two" as follows.

Column I

"VYDAC C-18 reversed phase: 10 μm, 300 Å, 4×250 mm".

Buffer A: 0.1% trifluoroacetic acid in water

Buffer B: 0.1% trifluoroacetic acid in acetonitrile

Column II

Mono Q HR 5/5 (Pharmacia).

Buffer A: Methanol-water (2:1)

Buffer B: Methanol-0.2M NaCl (2:1)

Gradients applied (flow rate):
1. 0–5 min.: 0–15% B; 5–30 min.: 15% B (1 ml/min.);
2. 0–5 min.: 0–15% B; 5–30 min.: 15% B (1.2 ml/min.);
3. 0–30 min.: 0–60% B; (1 ml/min.);
4. 0–5 min.: 0–6% B; 5–30 min.: 6% B; 30–35 min.: 6–18% B (1.2 ml/min.);
5. 0–5 min.: 0% B, 5–30 min.: 2% B (0.8 ml/min.).

The peptide content of the eluate was detected in UV light at 214 nm. Sample concentration: 1 mg/ml buffer A, injection volume: 25 μl.

Conditions of the HPLC analysis, the column and buffers (I or II) applied as well as the data of the gradients (1–5) are specified after the abbreviation in brackets, for instance HPLC(II/5).

The acyl-arginine aldehydes are present in equilibrium structures, i.e. in aldehyde, aldehyde hydrate and two aminocyclol forms. During HPLC analysis the aldehyde hydrate and one or both aminocyclol forms appear as separate peaks, consequently the products described in the examples can be specified by two or three k' values. 3-Cyclohexyl-D-lactyl-L-pipecolyl-L-arginine aldehyde hemisulfate of Example 9 represents an exception where six k' values corresponding to the six peaks are specified which are presumably due to the known cis-trans isomerization of the acyl-pipecolines.

EXAMPLE 1

D-Isochroman-1-carbonyl-L-prolyl-L-arginine aldehyde hemisulfate

Step 1: D-Isochroman-1-carbonyl-L-prolyl-$N^G$-benzyloxycarbonyl-L-arginine lactam 2.73 g (7 mmole) of t-butyloxycarbonyl-$N^G$-benzyloxycarbonyl-L-arginine lactam [S. Bajusz et al.: J. Med. Chem. 33 1729 (1990)] is suspended in 10 ml of chloroform, then 10 ml of ethyl acetate, saturated with HCl gas (0.11–0.15 g/ml), is added at constant stirring and ice cooling. After 2 hours the reaction mixture is diluted with 10–15 ml of diethyl ether, the crystal mass formed is filtered, washed with 5 ml of acetone and 5 ml of diethyl ether, then dried over potassium hydroxide at reduced pressure overnight. The $N^G$-benzyloxycarbonyl-L-arginine lactam hydrochloride obtained is dissolved in 10 ml of dimethyl formamide, cooled to −20° C. and added to the mixed anhydride below.

2.25 g (6 mmole) of D-isochroman-1-carbonyl-L-proline cyclohexylammonium salt (Example 1, Step D) is dissolved in 10 ml of ethyl acetate and 10 ml of 1M potassium hydrogen sulfate. The ethyl acetate layer is dried over sodium sulfate, then evaporated at 20–25 millibar from a water bath of about 40° C., finally further 5 ml of benzene is distilled off the residue which is dissolved in 6 ml of dimethyl formamide. The obtained solution is cooled to −20° C., then 0.66 ml (6 mmole) of N-methylmorpholine and 0.79 ml of isobutyl chloroformate are added at stirring. Stirring is continued for 10 minutes, then the above suspension of $N^G$-benzyloxycarbonyl-L-arginine lactam in dimethyl formamide and finally 2.1 ml (15 mmole) of triethylamine are added. The reaction mixture is stirred for 2 hours first at cooling, later it is left to warm up to room temperature. Thereafter the salt is filtered off, the filtrate is diluted with 50 ml of benzene, washed with 4×20 ml of water, 3×10 ml of 0.1M hydrochloric acid and again with 3×20 ml of water, dried over sodium sulfate and evaporated at 20–25 millibar from a water bath of about 40° C. The residue is dissolved in 1.5 ml of a mixture of ethyl acetate:pyridine:formic acid:water (240:20:6:5.5), transferred to a column prepared from 100 g of silica gel with ethyl acetate and eluted with a mixture of ethyl acetate:pyridine:formic acid:water (480:20:6:5.5). The fractions containing solely the pure product are pooled, shaken with 1/3 volume of 1M potassium hydrogen carbonate, the organic layer is washed to neutrality with water, dried over sodium sulfate and evaporated at 20–25 millibar from a water bath of about 40° C. The residue is dissolved in benzene, then repeatedly evaporated and treated with n-hexane.

Yield 2.3 g (70%), $R_f(7)=0.42-0.46$ $[\alpha]_D^{20}=-28.5°$ (c=1, tetrahydrofuran)

Analysis for $C_{29}H_{33}N_5O_6$ (547.59) Calculated: C %=63.60; H %=6.07; N %=12.79; Found: C %=63.5; H %=6.1; N %=12.5.

Step 2: D-Isochroman-1-carbonyl-L-prolyl-$N^G$-benzyloxycarbonyl-L-arginine aldehyde 1.64 g (3 mmole) of D-isochroman-1-carbonyl-L-prolyl-$N^G$-benzyloxycarbonyl-L-arginine lactam (Example 1, Step 1) is dissolved in 8 ml of tetrahydrofuran then 2.25 mmole of lithium aluminium hydride, dissolved in tetrahydrofuran, is added at a temperature not higher than −20° C. and at constant stirring. The progress of reduction is monitored by thin-layer chromatography using a developing solvent system of ethyl acetate:pyridine:acetic acid:water (240:20:6:11) and, if required, a further portion of lithium aluminium hydride is added. Then the reaction mixture is poured under cooling and stirring into 20 ml of cold 1M potassium hydrogen sulfate. The solution is diluted with 10 ml of water, then extracted with 2×10 ml of n-hexane and 3×10 ml of methylene chloride. The methylene chloride solutions are pooled, washed with 3×5 ml of water, 5% aqueous sodium hydrogen carbonate and again with water, dried over sodium sulfate and evaporated at 20–25 millibar from a water bath at about 40° C. The evaporation residue is treated with n-hexane.

Yield 1.15 g (70%), $R_f(3)=0.50-0.52$.

Step 3: D-Isochroman-1-carbonyl-L-prolyl-L-arginine aldehyde hemisulfate 0.82 g (1.5 mmole) of D-isochroman-1-carbonyl-L-prolyl-$N^G$-benzyloxycarbonyl-L-arginine aldehyde (Example 1, Step 2) is dissolved in 10 ml of 60% aqueous ethanol containing 0.75 mmole of sulfuric acid, then hydrogenated in the presence of Pd—C catalyst. The progress of the reaction is monitored by thin-layer chromatography in a developing solvent system of ethyl acetate:pyridine:acetic acid:water (45:20:6:11). The reaction is completed in about 30 minutes, then the catalyst is filtered off and washed with 60% aqueous ethanol and water. The filtrate is evaporated to about half of its volume at reduced pressure, then it is diluted with water to 10 ml. The solution is first extracted with methylene chloride, then it is freeze-dried. Yield: 0.5 g (70%).

$R_f(5)=0.48-0.52$; HPLC(I/1): k'=3.95, 4.76, 5.95.

$[\alpha]_D^{20}=-70.86°$ (c=1, 0.1M hydrochloric acid)

FAB mass spectrum (416 [M+H]$^+$) confirms the assumed structure.

The starting materials can be prepared as follows:

D-Isochroman-1-carbonyl-L-proline cyclohexylammonium salt

Step A: DL-Isochroman-1-carboxylic acid 12 ml (0.1 mole) of phenethyl alcohol and 10.12 g (0.11 mole) of glyoxylic acid hydrate are dissolved in 50 ml of trifluoroacetic acid. The solution is refluxed during 24 hours, then evaporated at 20–25 millibar from a water bath at max. 40° C. 100 ml of water and concentrated ammonium hydroxide in a volume sufficient to adjust the pH of the solution over 7 are added to the residue. The solution is extracted with 3×30 ml of diethyl ether, its pH is adjusted to about 3 with saturated potassium hydrogen sulfate, then the solution is extracted with 3×30 ml of ethyl acetate. The ethyl acetate solutions are pooled, washed to neutrality with water (3–4× 20 ml), dried over sodium sulfate and evaporated at 20–25 millibar from a water bath at about 40° C. The residue is treated with n-hexane, filtered, washed with n-hexane and air-dried.

Yield 10.7–11.6 g (60–65%)

$R_f(3)=0.65-0.75$; m.p.: 92°–93° C.

Analysis for $C_{10}H_{10}O_3$ (178.18) Calculated: C %=67.40; H %=5.66; Found: C %=67.45; H %=5.65.

Step B: DL-Isochroman-1-carbonyl-L-proline t-butyl ester 4.45 g (25 mmole) of DL-isochroman-1-carboxylic acid (Example 1, Step A) and 2.75 ml (25 mmole) of N-methylmorpholine are dissolved in 20 ml of dimethyl formamide. The solution is cooled to −15° C., then at this temperature and at stirring, first 3.3 ml of isobutyl chloroformate, then, after 10 minutes, the solution or suspension of 5.2 g (25 mmole) of L-proline t-butyl ester hydrochloride and 3.5 ml of triethylamine in 25 ml of dimethyl formamide, cooled to −15° C., are added. Stirring is continued for 2 hours, then the reaction mixture is filtered and evaporated at 15–20 millibar from a water bath at about 40° C. The residue is dissolved in about 30 ml of ethyl acetate and the solution are extracted with 3×20 ml of 0.25M sulfuric acid, water, 5% sodium hydrogen carbonate, again with water, dried over sodium sulfate and evaporated at 20–25 millibar from a water bath of about 40° C. The residue-DL-isochroman-1-carbonyl-L-proline t-butyl ester—is an oily product.

[R$_f$(7)=0.72 and 0.75].

Step C: DL-Isochroman-1-carbonyl-L-proline

The oily product prepared according to Example 1, Step B is dissolved in 25 ml of trifluoroacetic acid and left to stand at room temperature for 2 hours. Thereafter the solution is evaporated at 20–25 millibar from a water bath of about 40° C., the residue is dissolved in 30 ml of water and repeatedly evaporated. The residue obtained is dissolved in 50 ml of ethyl acetate and extracted with 3×30 ml of 5% sodium hydrogen carbonate. The sodium hydrogen carbonate solutions are pooled, its pH is adjusted to 3 with 1M potassium hydrogen sulfate and the solution is extracted with 3×30 ml of ethyl acetate. The ethyl acetate layers are pooled, dried over sodium sulfate and evaporated. The oily residue is the diastereomer pair comprising D- and L-isochroman-1-carbonyl-L-proline.

Yield 25 mmole, R$_f$(8)=0.40–0.42 and 0.51–0.53, resp.

Step D: D- and L-isochroman-1-carbonyl-L-proline cyclohexylammonium salt

The diastereomer pair obtained in Example 1, Step C is separated by silica gel column chromatography, applying 350 g of adsorbent and an eluent of ethyl acetate:pyridine:formic acid:water (480:20:6:5.5). The fractions containing solely compound F [top spot R$_f$(8)=0.51–0.53] and solely compound A [bottom spot R$_f$(8)=0.40–0.42] are pooled and processed by an identical method as follows.

The solution is evaporated in the usual manner (20–25 millibar, water bath temperature about 40° C.) to dryness and the residue is dissolved in 30 ml of methylene chloride. The thus-obtained solution is washed with 15% aqueous sodium chloride solution, dried and evaporated. The residual oil is dissolved in 20 ml of diethyl ether, then cyclohexylamine is added in an amount to render the solution mildly basic. The precipitated crystals of the cyclohexylammonium salt are filtered, washed with diethyl ether and dried under reduced pressure over concentrated sulfuric acid.

The product isolated from solution F is, according to its NMR spectrum, D-isochroman-1-carbonyl-L-proline cyclohexylammonium salt.

Yield 2.75 g (58.75%).

R$_f$(8)=0.54–0.59; m.p.: 122°–125° C.;

[α]$_D^{20}$=−41.5° (c=1, methanol).

Analysis for C$_{21}$H$_{30}$N$_2$O$_4$ (374.47) Calculated: C %=67.35; H %=8.07; N %=7.48; Found: C %=67.3; H %=8.15; N %=7.24.

The product isolated from solution A is, according to its NMR spectrum, L-isochroman-1-carbonyl-L-proline cyclohexylammonium salt.

Yield 3.1 g (66.3%).

R$_f$(8)=0.36–0.41; m.p.: 154°–157° C.;

[α]$_D^{20}$=−51.15° (c=1, methanol).

Analysis for c$_{21}$H$_{30}$N$_2$O$_4$ (374.47) Calculated: C %=67.35; H %=8.07; N %=7.48; Found: C %=66.39; H %=8.45; N %=7.435.

EXAMPLE 2

L-Isochroman-1-carbonyl-L-prolyl-L-arginine aldehyde hemisulfate

Step 1: L-Isochroman-1-carbonyl-L-prolyl-N$^G$-benzyloxycarbonyl-L-arginine lactam Applying 2.73 g (7 mmole) of t-butyloxycarbonyl-N$^G$-benzyloxycarbonyl-L-arginine lactam [S. Bajusz et al.: J. Med. Chem. 33, 1729 (1990)] and 2.25 g (6 mmole) of L-isochroman-1-carbonyl-L-proline cyclohexylammonium salt (Example 1, Step D) as starting compounds, and using the process described in Example 1, Step 1 in every respect, utilizing identical amounts of solvents and reagents, 2.3 g (70%) of the aimed product is obtained.

R$_f$(7)=0.42–0.46.

[α]$_D^{20}$=−70.3° (c=1, tetrahydrofuran)

Analysis for C$_{29}$H$_{33}$N$_5$O$_6$ (547.59) Calculated: C %=63.60; H %=6.07; N %=12.79; Found: C %=63.3; H %=6.2; N %=12.4.

Step 2: L-Isochroman-1-carbonyl-L-prolyl-N$^G$-benzyloxycarbonyl-L-arginine aldehyde 1.64 g (3 mmole) of L-isochroman-1-carbonyl-L-prolyl-N$^G$-benzyloxycarbonyl-L-arginine lactam (Example 2, Step 1) is transformed by the process described in Example 1, Step 2, using identical amounts of solvents and reagents.

Yield 1.15 g (70%)

R$_f$(3)=0.48–0.50.

Step 3: L-Isochroman-1-carbonyl-L-prolyl-L-arginine aldehyde hemisulfate 0.82 g (1.5 mmole) of L-isochroman-1-carbonyl-L-prolyl-N$^G$-benzyloxycarbonyl-L-arginine aldehyde (Example 2, Step 2) is transformed by the process described in Example 1, Step 3, using identical amounts of solvents and reagents.

Yield 0.5 g (70%)

R$_f$(5)=0.48–0.52; HPLC(I/1): k'=3.90, 4.62, 5.29.

[α]$_D^{20}$=−55.2° (c=1, 0.1M hydrochloric acid).

FAB mass spectrum (416 [M+H]$^+$) confirms the assumed structure.

EXAMPLE 3

D-Isochroman-3-carbonyl-L-prolyl-L-arginine aldehyde hemisulfate

Step 1: D-Isochroman-3-carbonyl-L-prolyl-N$^G$-benzyloxycarbonyl-L-arginine lactam Applying 2.73 g (7 mmole) of t-butyloxycarbonyl-N$^G$-benzyloxycarbonyl-L-arginine lactam [S. Bajusz et al.: J. Med. Chem. 33, 1729 (1990)] and 2.25 g (6 mmole) of D-isochroman-3-carbonyl-L-proline cyclohexylammonium salt (Example 3, Step C) as starting compounds, and using the process described in Example 1, Step 1 in every respect—utilizing identical amounts of solvents and reagents—yields 2.3 g (70%) of the product.

R$_f$(9)=0.45–0.55.

[α]$_D^{20}$=−50° (c=1, tetrahydrofuran)

Analysis for C$_{29}$H$_{33}$N$_5$O$_6$ (547.59) Calculated: C %=63.60; H %=6.07; N %=12.79; Found: C %=63.8; H %=6.2; N %=12.5.

Step 2: D-Isochroman-3-carbonyl-L-prolyl-N$^G$-benzyloxycarbonyl-L-arginine aldehyde 2.2 g (4 mmole) of D-isochroman-3-carbonyl-L-prolyl-N$^G$-benzyloxycarbonyl-L-arginine lactam (Example 3, Step 1) is transformed by the process described in Example 1, Step 2, using identical amounts of solvents and reagents.

Yield 1.55 g (70%)

R$_f$(2)=0.15–0.25.

[α]$_D^{20}$=−28.6° (c=1, tetrahydrofuran)

Step 3: D-Isochroman-3-carbonyl-L-prolyl-L-arginine aldehyde hemisulfate 1.1 g (2 mmole) of D-isochroman-3-carbonyl-L-prolyl-N$^G$-benzyloxycarbonyl-L-arginine aldehyde (Example 3, Step 2) is transformed by the process described in Example 1, Step 3, using identical amounts of solvents and reagents.

Yield 0.67 g (70%)

R$_f$(4)=0.20–0.30; HPLC(I/1): k'=4.55, 5.65, 6.95.

FAB mass spectrum (416 [M+H]$^+$) confirms the assumed structure.

The starting materials can be prepared as follows:

D-Isochroman-3-carbonyl-L-proline cyclohexylammonium salt

Step A: D-Isochromane-3-carboxylic acid

To 3 g of paraformaldehyde dissolved in 50 ml of trifluoroacetic acid 16.6 g (0.1 mole) of 3-phenyl-D-lactic acid [M. Winitz et al.: J. Am. Chem. Soc. 82 2423 (1956)] is added. The solution is refluxed for 48 hours, then it is evaporated at 20–25 millibar from a water bath of about 40° C. Further 50 ml of water is distilled off, thereafter the crystalline product formed is recrystallized from water. The crystals are filtered, washed with water and dried at reduced pressure over phosphorus pentoxide.

Yield 14.2–16.0 g (80–90%)
$R_f(1)=0.40-0.50$; m.p.: 86°–88° C.
$[\alpha]_D^{20}=+149°$ (c=1, methanol)
Analysis for $C_{10}H_{10}O_3$ (178.18) Calculated: C %=67.4; H %=5.66; Found: C %=67.4; H %=5.65;

Step B: D-Isochroman-3-carbonyl-L-proline t-butyl ester

4.45 g (25 mmole) of D-isochroman-3-carboxylic acid (Example 3, Step A) and 5.2 g (25 mmole) of L-proline t-butyl ester hydrochloride are condensed according to the process described in Example 1, Step B, applying identical amounts of solvents and reagents. The oily product is D-isochroman-3-carbonyl-L-proline t-butyl ester.

Yield 25 mmole.
$R_f(1)=0.80-0.90$.

Step C: D-Isochroman-3-carbonyl-L-proline cyclohexylammonium salt

The oily product of Example 3, Step B is dissolved in 25 ml of trifluoroacetic acid and left to stand at room temperature for 2 hours. The trifluoroacetic acid solution is evaporated at 20–25 millibar from a water bath at about 40° C., the residue is dissolved in 30 ml of water and repeatedly evaporated. 50 ml of water and solid sodium hydrogen carbonate in an amount to adjust the pH over 7 are added to the oily residue. The solution is extracted with 3×10 ml of ethyl acetate, then the solution is acidified to pH 3 with 1M potassium hydrogen sulfate and extracted with 3×30 ml of ethyl acetate. After drying over sodium sulfate the ethyl acetate extracts are evaporated. The oily evaporation residue is dissolved in 20 ml of diethyl ether, then cyclohexylamine is added in an amount to render the solution slightly alkaline. The precipitated crystal mass of the cyclohexylammonium salt is filtered, washed with diethyl ether and dried at reduced pressure over concentrated sulfuric acid.

Yield 6.5 g (70%)
$R_f(1)=0.30-0.40$; m.p.: 158°–160° C.
$[\alpha]_D^{20}=-3.5°$ (c=1, methanol)
Analysis for $C_{21}H_{30}N_2O_4$ (374.47) Calculated: C %=67.35; H %=8.07; N %=7.48; Found: C %=67.4; H %=8.4; N %=7.3.

EXAMPLE 4

L-Isochroman-3-carbonyl-L-prolyl-L-arginine aldehyde hemisulfate

Step 1: L-Isochroman-3-carbonyl-L-prolyl-$N^G$-benzyloxycarbonyl-L-arginine lactam

Applying 2.73 g (7 mmole) of t-butyloxycarbonyl-$N^G$-benzyloxycarbonyl-L-arginine lactam [S. Bajusz et al.: J. Med. Chem. 33, 1729 (1990)] and 2.25 g (6 mmole) of L-isochroman-3-carbonyl-L-proline cyclohexylammonium salt (Example 4, Step C) as starting compounds and using the process described in Example 1, Step 1 in every respect—utilizing identical amounts of solvents and reagents—yields 2.3 g (70%) of the aimed product.

$R_f(9)=0.50-0.60$.

Step 2: L-Isochroman-3-carbonyl-L-prolyl-$N^G$-benzyloxycarbonyl-L-arginine aldehyde

2.2 g (4 mmole) of L-isochroman-3-carbonyl-L-prolyl-$N^G$-benzyloxycarbonyl-L-arginine lactam (Example 4, Step 1) is transformed by the process described in Example 1, Step 2, using proportional amounts of solvents and reagents.

Yield 1.55 g (70%)
$R_f(2)=0.20-0.30$.

Step 3: L-Isochroman-3-carbonyl-L-prolyl-L-arginine aldehyde hemisulfate

1.1 g (2 mmole) of L-isochroman-3-carbonyl-L-prolyl-$N^G$-benzyloxycarbonyl-L-arginine aldehyde (Example 4, Step 2) is transformed by the process described in Example 1, Step 3, using proportional amounts of solvents and reagents.

Yield 0.67 g (70%)
$R_f(4)=0.25-0.35$; HPLC(I/1): k'=4.65, 5.40, 6.65.
FAB mass spectrum (416 $[M+H]^+$) confirms the assumed structure.

The starting materials can be prepared as follows:

L-Isochroman-3-carbonyl-L-proline cyclohexylammonium salt

Step A: L-Isochroman-3-carboxylic acid

1.5 g of paraformaldehyde and 8.3 g (50 mmole) of 3-phenyl-L-lactic acid [M. Winitz et al.: J. Am. Chem. Soc. 82, 2423 (1956)] are condensed according to the process described in Example 3, Step A, using proportional amounts of solvents and reagents.

Yield 7.1–8.0 g (80–90%)
$R_f(1)=0.40-0.50$; m.p.: 86°–88° C.
$[\alpha]_D^{20}=-149°$ (c=1, methanol)
Analysis for $C_{10}H_{10}O_3$ (178.18) Calculated: C %=67.4; H %=5.66; Found: C %=67.4; H %=5.65.

Step B: L-Isochroman-3-carbonyl-L-proline t-butyl ester

10 4.45 g (25 mmole) of L-isochroman-3-carboxylic acid [Example 4, Step A] and 5.2 g (25 mmole) of L-proline t-butyl ester hydrochloride are condensed according to the process described in Example 1, Step B, applying identical amounts of solvents and reagents. The oily product is L-isochroman-3-carbonyl-L-proline t-butyl ester.

Yield 25 mmole.
$R_f(1)=0.80-0.90$.

Step C: L-Isochroman-3-carbonyl-L-proline cyclohexylammonium salt

The oily product of Example 4, Step B is transformed according to the process described in Example 3, Step C, using identical amounts of solvents and reagents.

Yield 6.5 g (70%)
$R_f(1)=0.40-0.50$; m.p.: 148°–150° C.
$[\alpha]_D^{20}=-91.9°$ (c=1, methanol)
Analysis for $C_{21}H_{30}N_2O_4$ (374.47) Calculated: C %=67.35; H %=8.07; N %=7.48; Found: C %=67.2; H %=8.0; N %=7.4.

EXAMPLE 5

3-Phenyl-D-lactyl-L-prolyl-L-arginine aldehyde hemisulfate

Step 1: O-Tetrahydropyranyl-3-phenyl-D-lactyl-L-prolyl-$N^G$-benzyloxycarbonyl-L-arginine lactam

2.68 g (6 mmole) of O-tetrahydropyranyl-3-phenyl-D-lactyl-L-proline cyclohexylammonium salt (Example 5, Step B) is dissolved in 30 ml of dichloromethane and 7 ml of 1M potassium hydrogen sulfate. The dichloromethane layer is washed with water, dried over sodium sulfate and evaporated at 20–25 millibar from a water bath at about 40°

C. Transforming the residue and 2.73 g (7 mmole) of t-butyloxycarbonyl-$N^G$-benzyloxycarbonyl-L-arginine lactam [S. Bajusz et al.: J. Med. Chem. 33, 1729 (1990)] yields 2.3 g (65%) of the aimed product.

$R_f$(ethyl acetate)=0.55–0.65.

Analysis for $C_{33}H_{41}N_5O_7$ (619.70) Calculated: C %=63.95; H %=6.67; N %=11.3; Found: C %=63.8; H %=6.7; N %=11.1.

Step 2: O-Tetrahydropyranyl-3-phenyl-D-lactyl-L-prolyl-$N^G$-benzyloxycarbonyl-L-arginine aldehyde Transforming 2.2 g (3.5 mmole) of O-tetrahydropyranyl-3-phenyl-D-lactyl-L-prolyl-$N^G$-benzyloxycarbonyl-L-arginine lactam (Example 5, Step 1) according to the process described in Example 1, Step 2 by using proportional amounts of solvents and reagents, 1.30 g (60%) of the aimed product is obtained.

$R_f$(2)=0.40–0.50.

Analysis for $C_{33}H_{43}N_5O_7$ (621.71) Calculated: C %=63.75; H %=6.97; N %=11.26; Found: C %=63.85; H %=7.1; N %=11.1.

Step 3: 3-Phenyl-D-lactyl-L-prolyl-L-arginine aldehyde hemisulfate

Transforming 1.25 g (2 mmole) of O-tetrahydropyranyl-3-phenyl-D-lactyl-L-prolyl-$N^G$-benzyloxycarbonyl-L-arginine aldehyde (Example 5, Step 2) according to the process described in Example 7, Step 3, using proportional amounts of solvents and reagents, 0.6 g (60%) of the aimed product is obtained.

$R_f$(5)=0.50–0.60; HPLC(I/1): k'=3.96, 4.96.

FAB mass spectrum (404 [M+H]$^+$) confirms the assumed structure.

The starting materials can be prepared as follows:

O-Tetrahydropyranyl-3-phenyl-D-lactyl-L-proline cyclohexylammonium salt

Step A: O-Tetrahydropyranyl-3-phenyl-D-lactic acid cyclohexylammonium salt 6.64 g (40 mmole) of 3-phenyl-D-lactic acid and 3.7 g (44 mmole) of dihydropyran are reacted in acetonitrile according to the method of Obrecht and Heimgartner [Helv. Chim. Acta 67, 526 (1984)]. The reaction mixture is evaporated at 20–25 millibar from a water bath at about 40° C. The residue is dissolved in 20 ml of dichloromethane, washed with water, dried over sodium sulfate and repeatedly evaporated. The obtained O-tetrahydropyranyl-3-phenyl-D-lactic acid is dissolved in diethyl ether and converted into cyclohexylammonium salt. The crystals are filtered off, washed with diethyl ether and dried at reduced pressure.

Yield 8.4 g (60%)

$R_f$(9)=0.68–0.77; m.p.: 148°–150° C.

Analysis for $C_{20}H_{31}NO_4$ (349.46) Calculated: C %=68.74; H %=8.94; N %=4.01; Found: C %=68.65; H %=9.1; N %=4.1.

Step B: O-Tetrahydropyranyl-3-phenyl-D-lactyl-L-proline cyclohexylammonium salt 8.74 g (25 mmole) of O-tetrahydropyranyl-3-phenyl-D-lactic acid cyclohexylammonium salt (Example 5, Step A) is dissolved in 30 ml of 1M potassium hydrogen sulfate and 50 ml of dichloromethane. The dichloromethane layer is washed with water, dried over sodium sulfate and evaporated at 20–25 millibar from a water bath at about 40° C. The obtained O-tetrahydropyranyl-3-phenyl-D-lactic acid and 4.15 g (25 mmole) of L-proline methyl ester hydrochloride are condensed by the method of Obrecht and Heimgartner [Helv. Chim. Acta 67, 526 (1984)], the O-tetrahydropyranyl-3-phenyl-D-lactyl-L-proline methyl ester formed is saponified and the resulting O-tetrahydropyranyl-3-phenyl-D-lactyl-L-proline is converted in diethyl ether solution to the crystalline cyclohexylammonium salt.

Yield 6.7 g (60%)

$R_f$(1)=0.3–0.4

Analysis for $C_{25}H_{38}N_2O_5$ (446.57) Calculated: C %=67.23; H %=8.58; N %=6.27; Found: C %=67.3; H %=8.7; N %=6.1.

EXAMPLE 6

D-2-Phenyl-2-hydroxyacetyl-L-prolyl-L-arginine aldehyde hemisulfate

Step 1: O-Tetrahydropyranyl-D-2-phenyl-2-hydroxyacetyl-L-prolyl-$N^G$-benzyloxycarbonyl-L-arginine lactam Starting from 2.6 g (6 mmole) of O-tetrahydropyranyl-D-2-phenyl-2-hydroxyacetyl-L-proline cyclohexylammonium salt (Example 6, Step B) and 2.73 g (7 mmole) of t-butyloxycarbonyl-$N^G$-benzyloxycarbonyl-L-arginine lactam [S. Bajusz et al.: J. Med. Chem. 33, 1729 (1990)] and applying the process described in Example 5, Step 1 in every respect, by using identical amounts of solvents and reagents, 2.5 g (69%) of the oily product is obtained which is directly used in the subsequent step. [$R_f$(ethyl acetate)=0.5–0.6].

Step 2: O-Tetrahydropyranyl-D-2-phenyl-2-hydroxyacetyl-L-prolyl-$N^G$-benzyloxycarbonyl-L-arginine aldehyde Transforming 2.5 g (4.1 mmole) of O-tetrahydropyranyl-D-2-phenyl-2-hydroxyacetyl-L-prolyl-$N^G$-benzyloxycarbonyl-L-arginine lactam (Example 6, Step 1) according to the process described in Example 5, Step 2, using proportional amounts of solvents and reagents, 1.50 g (60%) of the aimed product is obtained.

$R_f$(2)=0.33–0.44

Analysis for $C_{32}H_{41}N_5O_7$ (607.69) Calculated: C %=63.24; H %=6.80; N %=11.52; Found: C=63.1; H %=6.9; N %=11.35.

Step 3: D-2-Phenyl-2-hydroxyacetyl-L-prolyl-L-arginine aldehyde hemisulfate

Transforming 1.22 g (2 mmole) of O-tetrahydropyranyl-D-2-phenyl-2-hydroxyacetyl-L-prolyl-$N^G$-benzyloxycarbonyl-L-arginine aldehyde (Example 6, Step 2) according to the process described in Example 7, Step 3, using proportional amounts of solvents and reagents, 0.6 g (60%) of the aimed product is obtained.

$R_f$(5)=0.46–0.56; HPLC(I/4): k'=8.33, 9.22, 14.20.

FAB mass spectrum (390 [M+H]$^+$) confirms the assumed structure.

The starting materials can be prepared as follows:

O-Tetrahydropyranyl-D-2-phenyl-2-hydroxyacetyl-L-proline cyclohexylammonium salt Step A: O-Tetrahydropyranyl-D-2-phenyl-2-hydroxyacetic acid cyclohexylammonium salt Transforming 6.1 g (40 mmole) of D-mandelic acid according to the process described in Example 5, Step A, using identical amounts of solvents and reagents, 8.4 g (62%) of the aimed product is obtained.

$R_f$(9)=0.68–0.77; m.p.: 148°–150° C.

Analysis for $C_{19}H_{29}NO_4$ (335.43) Calculated: C %=68.03; H %=8.71; N %=4.18; Found: C %=67.95; H %=8.8; N %=4.1.

Step B: O-Tetrahydropyranyl-D-2-phenyl-2-hydroxyacetyl-L-proline cyclohexylammonium salt Transforming 8.4 g (25 mmole) of O-tetrahydropyranyl-D-2-phenyl-2-hydroxyacetic acid cyclohexylammonium salt (Example 6, Step A) and 4.15 g (25 mmole) of L-proline methyl ester hydrochloride according to the process described in Example 5, Step B, by using identical amounts of solvents and reagents, 6.7 g (62%) of the aimed product is obtained.

$R_f$(1)=0.3–0.4.

Analysis for $C_{24}H_{36}N_2O_5$ (432.54) Calculated: C %=66.64; H %=8.39; N %=6.48; Found: C %=66.5; H %=8.25; N %=6.3.

EXAMPLE 7

3-Cyclohexyl-D-lactyl-L-prolyl-L-arginine aldehyde hemisulfate

Step 1: O-Tetrahydropyranyl-3-cyclohexyl-D-lactyl-L-prolyl-$N^G$-benzyloxycarbonyl-L-arginine lactam 2.72 g (6 mmole) of O-tetrahydropyranyl-3-cyclohexyl-D-lactyl-L-proline cyclohexylammonium salt (Example 7, Step D) is dissolved in 30 ml of dichloromethane and 7 ml of 1M potassium hydrogen sulfate. The dichloromethane layer is washed with water, dried over sodium sulfate and evaporated from a water bath at about 40° C. and 20–25 millibar. Reacting the residue and 2.73 g (7 mmole) of t-butyloxycarbonyl-$N^G$-benzyloxycarbonyl-L-arginine lactam [S. Bajusz et al.: J. Med. Chem. 33, 1729 (1990)] according the procedure described in Example 1, Step 1, applying identical amounts of solvents and reagents, 2.44 g (65%) of the aimed product is obtained.

$R_f(2)$=0.73–0.80

Step 2: O-Tetrahydropyranyl-3-cyclohexyl-D-lactyl-L-prolyl-$N^G$-benzyloxycarbonyl-L-arginine aldehyde 2.2 g (3.5 mmole) of O-tetrahydropyranyl-3-cyclohexyl-D-lactyl-L-prolyl-$N^G$-benzyloxycarbonyl-L-arginine lactam (Example 7, Step 1) is dissolved in 8 ml of tetrahydrofuran, then a solution of 2.625 mmole of lithium aluminium hydride, dissolved in tetrahydrofuran, is added at a temperature of –50° C., under constant stirring. The progress of the reduction is monitored by thin-layer chromatography in a developing solvent system of ethyl acetate:pyridine:acetic acid:water (240:20:6:11). If required, further portions of lithium aluminium hydride are added. The reaction mixture is acidified to pH 3 with 1M potassium hydrogen sulfate under cooling and stirring. The solution is diluted with water up to the point when it turns cloudy (approx. 10 ml), washed with 2×10 ml of a mixture of n-hexane:ethyl acetate (1:1) and extracted with 3×10 ml of methylene chloride. The methylene chloride layers are pooled, washed with 3×5 ml of water, 5% aqueous sodium hydrogen carbonate, then again with water, dried over sodium sulfate and evaporated from a water bath at about 40° C., at 20–25 millibar. The evaporation residue is worked up with n-hexane, filtered and dried at reduced pressure.

Yield 1.30 g (59%).

$R_f(2)$=0.26–0.38.

Analysis for $C_{33}H_{49}N_5O_7$ (627.76) Calculated: C %=63.13; H %=7.87; N %=11.16 Found: C %=63.3; H %=8.0; N %=11.0.

Step 3: 3-Cyclohexyl-D-lactyl-L-prolyl-L-arginine aldehyde hemisulfate 1.25 g (2 mmole) of O-tetrahydropyranyl-3-cyclohexyl-D-lactyl-L-prolyl-$N^G$-benzyloxycarbonyl-L-arginine aldehyde (Example 7, Step 2) is dissolved in 10 ml of 60% aqueous ethanol containing 1.05 mmole of sulfuric acid and submitted to hydrogenation in the presence of a Pd—C catalyst. The progress of the reaction is monitored by thin-layer chromatography in a developing solvent system of ethyl acetate:pyridine:acetic acid:water (45:20:6:11) ($R_f$= 0.45–0.54; intermediate product free from benzyloxycarbonyl group). The reaction is completed in about 60 minutes, then the catalyst is filtered off and washed with 60% aqueous ethanol and water. The filtrate is concentrated to about half of its volume at reduced pressure, diluted with water to 10 ml, its pH is adjusted to 2.8 with sulfuric acid or an anion-exchange resin (HO⁻) and then it is left to stand at room temperature for about 24 hours till the complete cleavage of the tetrahydropyranyl protecting group (reaction is monitored by thin-layer chromatography in the above solvent system). The aqueous solution is washed with 3×5 ml of methylene chloride, the pH is adjusted to 3.6 with an anion-exchange resin (HO⁻), then the solution is frozen and freeze-dried.

Yield 0.6 g (60%)

$R_f(5)$=0.43–0.51; HPLC(I/3): k'=35.25 and 37.40

FAB mass spectrum (410 [M+H]⁺) confirms the assumed structure.

The starting materials can be prepared as follows:

O-Tetrahydropyranyl-3-cyclohexyl-D-lactyl-L-proline cyclohexylammonium salt

Step A: 3-Cyclohexyl-D-lactic acid 5 g (30.1 mmole) of 3-phenyl-D-lactic acid [$R_f(2)$= 0.45–0.55] is dissolved in 70 ml of acetic acid and submitted to hydrogenation in the presence of 0.25 g of platinum(IV) oxide catalyst in the temperature range of 40° to 50° C. The reaction is monitored by thin-layer chromatography [final product: $R_f(2)$=0.6–0.7]. After completed reaction the catalyst is filtered off, the filtrate is evaporated from a water bath at a temperature not higher than 40° C., at 20–25 millibar. Then 20 ml of toluene is evaporated twice from the residue which is finally recrystallized from n-hexane.

Yield 4.3 g (83%)

$R_f(2)$=0.60–0.70; m.p.: 90°–93° C.

$[\alpha]_D^{20}$=+8.45° (c=1, methanol)

Analysis for $C_9H_{16}O_3$ (172.22) Calculated: C %=62.76; H %=9.36; Found: C %=62.65; H %=9.5;

Step B: 3-Cyclohexyl-D-lactic acid methyl ester 3.44 g (20 mmole) of 3-cyclohexyl-D-lactic acid (Example 7, Step A) [$R_f(9)$=0.40–0.45] is dissolved in 30 ml of anhydrous methanol, 4 drops of concentrated sulfuric acid are added, and the mixture is refluxed for 3 hours. The solution is evaporated from a water bath at a temperature not exceeding 40° C., at 20–25 millibar, the residue is dissolved in 40 ml of methylene chloride and washed with water to neutrality. The methylene chloride solution is dried over sodium sulfate and evaporated under conditions described above. In this way 3.8 g (20 mmole) of 3-cyclohexyl-D-lactic acid methyl ester [$R_f(9)$=0.80–0.86] is obtained as an oil.

Step C: O-Tetrahydropyranyl-3-cyclohexyl-D-lactic acid cyclohexylammonium salt 20 mmole of 3-cyclohexyl-D-lactic acid methyl ester (Example 7, Step B) is dissolved in 20 ml of methylene chloride, then 2 ml (22 mmole) of dihydropyran and 0.3 ml of ethyl acetate containing hydrogen chloride (concentration: 0.11–0.15 g/ml) are added at constant stirring. The solution is left to stand at room temperature overnight, thereafter it is diluted with 20 ml of methylene chloride, washed with water to neutrality and evaporated from a water bath at a temperature not exceeding 40° C., at 20–25 millibar. The resulting oil [4.4 g of O-tetrahydropyranyl-3-cyclohexyl-D-lactic acid methyl ester, $R_f(9)$=0.84–0.90] is dissolved in 40 ml of methanol, then 20 ml of 1M sodium hydroxide is added. The reaction mixture is left to stand at room temperature overnight, thereafter 20 ml of water is added and the solution is concentrated from a water bath at a temperature not higher than 40° C., at 20–25 millibar up to the appearance of mild cloudiness. The solution obtained is washed with 10 ml of methylene chloride, cooled to 5°–10° C., the pH is adjusted to 3 with 1M potassium hydrogen sulfate and extracted with 3×10 ml of methylene chloride. The methylene chloride layers are pooled, washed with water to neutrality, dried over sodium sulfate and evaporated under conditions mentioned above. The O-tetrahydropyranyl-3-cyclohexyl-D-lactic acid obtained is dissolved in diethyl ether and converted to cyclohexylammonium salt. The crystals are filtered off, washed with diethyl ether and dried at reduced pressure.

Yield 5.0 g (70%)

M.p.: 153°–155° C. (sintering at 142° C.).

$R_f(9)=0.63–0.70$;

Analysis for $C_{20}H_{37}NO_4$ (355.50) Calculated: C %=67.57; H %=10.49; N %=3.98; Found: C %=68.0; H %=11.0; N %=3.85.

Step D: O-Tetrahydropyranyl-3-cyclohexyl-D-lactyl-L-proline cyclohexylammonium salt 4.45 g (12.5 mmole) of O-tetrahydropyranyl-3-cyclohexyl-D-lactic acid cyclohexylammonium salt (Example 7, Step C) is dissolved in 15 ml of a 1M solution of potassium hydrogen sulfate and 25 ml of methylene chloride. The methylene chloride layer is washed with water, dried over sodium sulfate and evaporated from a water bath at a temperature not exceeding 40° C., at 20–25 millibar. The resulting O-tetrahydropyranyl-3-cyclohexyl-D-lactic acid is dissolved in 15 ml of dimethyl formamide, the solution is cooled in ice water, then 2.06 g (12.5 mmole) of L-proline methyl ester hydrochloride, 2.10 g (13.75 mmole) of 1-hydroxybenzotriazole hydrate, 1.75 ml of triethylamine (12.5 mmole) and 2.58 g (12.5 mmole) of dicyclohexylcarbodiimide are added. The reaction mixture is left to stand overnight at room temperature, the precipitated dicyclohexylurea is filtered and the filtrate is evaporated from a water bath at a temperature not exceeding 40° C., at 20–25 millibar. The residue is dissolved in 30 ml of methylene chloride, washed with 10 ml of water, 2×10 ml of 5% sodium hydrogen carbonate solution and again with water, dried over sodium sulfate and evaporated from a water bath at about 40° C. and 20–25 millibar. The resulting oil [O-tetrahydropyranyl-3-cyclohexyl-D-lactyl-L-proline methyl ester, $R_f(9)=0.86–0.93$] is dissolved in 40 ml of methanol, 13 ml of a solution of 1M sodium hydroxide is added and the mixture is stirred for 24 hours. Thereafter 15 ml of a 1M sodium hydroxide solution and 20 ml of methylene chloride are added. The two layers formed are separated, the aqueous phase is acidified to pH 3 with 1M potassium hydrogen sulfate under constant stirring and ice cooling and extracted with 2×15 ml of methylene chloride. The methylene chloride layers are pooled, washed with water to neutrality, dried over sodium sulfate and evaporated under conditions described above. The resulting O-tetrahydropyranyl-3-cyclohexyl-D-lactyl-L-proline is converted to the crystalline cyclohexylammonium salt in diethyl ether solution.

Yield 3.2 g (56%); m.p.: 119°–120° C.

$R_f(9)=0.44–0.51$

Analysis for $C_{25}H_{44}N_2O_5$ (452.62) Calculated: C %=66.34; H %=9.80; N %=6.19; Found: C %=66.4; H %=9.9; N %=6.25.

EXAMPLE 8

D-2-Cyclohexyl-2-hydroxyacetyl-L-prolyl-L-arginine aldehyde hemisulfate

Step 1: O-Tetrahydropyranyl-D-2-cyclohexyl-2-hydroxyacetyl-L-prolyl-$N^G$-benzyloxycarbonyl-L-arginine lactam Starting from 2.6 g (6 mmole) of O-tetrahydropyranyl-D-2-cyclohexyl-2-hydroxyacetyl-L-proline cyclohexylammonium salt (Example 8, Step C) and 2.73 g (7 mmole) of t-butyloxycarbonyl-$N^G$-benzyloxycarbonyl-L-argninine lactam [S. Bajusz et al.: J. Med. Chem. 33, 1729 (1990)] the procedure described in Example 5, Step 1 is applied, using identical amounts of solvents and reagents.

Yield: 2.53 g (69%)

$R_f(2)=0.70–0.78$.

Step 2: O-Tetrahydropyranyl-D-2-cyclohexyl-2-hydroxyacetyl-L-prolyl-$N^G$-benzyloxycarbonyl-L-arginine aldehyde 2.15 g (3.5 mmole) of O-tetrahydropyranyl-D-2-cyclohexyl-2-hydroxyacetyl-L-prolyl-$N^G$-benzyloxycarbonyl-L-arginine lactam (Example 8, Step 1) is transformed according to the process described in Example 7, Step 2, applying identical amounts of solvents and reagents.

Yield: 1.40 g (65%)

$R_f(2)=0.23–0.31$

Analysis for $C_{32}H_{47}N_5O_7$ (613.74) Calculated: C %=62.62; H %=7.72; N %=11.41 Found: C %=62.8; H %=7.8; N %=11.2.

Step 3: D-2-Cyclohexyl-2-hydroxyacetyl-L-prolyl-L-arginine aldehyde hemisulfate 1.23 g (2 mmole) of O-tetrahydropyranyl-D-2-cyclohexyl-2-hydroxyacetyl-L-prolyl-$N^G$-benzyloxycarbonyl-L-arginine aldehyde (Example 8, Step 2) is transformed according to the process described in Example 7, Step 3, applying identical amounts of solvents and reagents.

Yield: 0.6 g (60%)

$R_f(5)=0.39–0.46$.

HPLC(I/3): k'=5.70, 6.10 and 8.76.

FAB mass spectrum confirms the assumed structure (396 $[M+H]^+$).

The starting material can be prepared as follows:

O-Tetrahydropyranyl-D-2-cyclohexyl-2-hydroxyacetyl-L-proline cyclohexylammonium salt Step A: D-2-Cyclohexyl-2-hydroxyacetic acid methyl ester Starting from 3.2 g (20 mmole) of D-2-cyclohexyl-2-hydroxyacetic acid [H. Lettré, H. Barnback and H. Staunau: Chem Ber. 69, 1594–1598 (1936) [$R_f(9)=0.32–0.42$] and following the process described in Example 7, Step B, applying identical amounts of solvents and reagents, 3.5 g (20 mmole) of an oily product [$R_f(9)=0.78–0.84$], considered to be D-2-cyclohexyl-2-hydroxyacetic acid methyl ester, is obtained.

Step B: O-Tetrahydropyranyl-D-2-cyclohexyl-2-hydroxyacetic acid cyclohexylammonium salt Starting from 20 mmole of D-2-cyclohexyl-2-hydroxyacetic acid methyl ester (Example 8, Step A) and following the process described in Example 7, Step C, applying identical amounts of solvents and reagents, 4.1 g of an oily intermediary product O-tetrahydropyranyl-D-2-cyclohexyl-2-hydroxyacetic acid methyl ester [$R_f(9)=$ 0.80–0.88], then the aimed product is obtained.

Yield: 4.1 g (60%)

$R_f(9)=0.55–0.70$

M.p.: 152°–155° C. (sintering at 122° C.)

Analysis for $C_{19}H_{35}NO_4$ (341.48) Calculated: C %=66.82; H %=10.33; N %=4.10; Found: C %=66.9; H %=10.3; N %=4.2.

Step C: O-Tetrahydropyranyl-D-2-cyclohexyl-2-hydroxyacetyl-L-proline cyclohexylammonium salt Starting from 4.3 g (12.5 mmole) of O-tetrahydropyranyl-D-2-cyclohexyl-2-hydroxyacetic acid cyclohexylammonium salt (Example 8, Step B) and 2.1 g (12.5 mmole) of L-proline methyl ester hydrochloride and proceeding according to the process described in Example 7, Step D, applying identical amounts of solvents and reagents, the oily intermediary product O-tetrahydropyranyl-D-2-cyclohexyl- 2-hydroxyacetyl-L-proline methyl ester [$R_f(9)$=0.84–0.93], then the aimed product is obtained.

Yield: 3.25 g (60%)
$R_f(9)$=0.20–0.27; m.p.: 140°–142° C.
Analysis for $C_{24}H_{42}N_2O_5$ (438.61) Calculated: C %=65.72; H %=9.65; N %=6.39; Found: C %=65.7; H %=9.7; N %=6.3.

EXAMPLE 9

3-Cyclohexyl-D-lactyl-L-pipecolyl-L-arginine aldehyde hemisulfate

Step 1: O-Tetrahydropyranyl-3-cyclohexyl-D-lactyl-L-pipecolyl-$N^G$-benzyloxycarbonyl-L-arginine lactam 3.9 g (10 mmole) of t-butyloxycarbonyl-$N^G$-benzyloxycarbonyl-L-arginine lactam [S. Bajusz et al.: J. Med. Chem. 33, 1729 (1990)) is suspended in 15 ml of chloroform, then 14.5 ml of ethyl acetate containing hydrogen chloride gas (concentration 0.11–0.15 g/ml) are added under stirring and cooling in ice water. After two hours the reaction mixture is diluted with 15–20 ml of diethyl ether, the crystals formed are filtered off, washed with 7 ml of acetone and 7 ml of diethyl ether and dried over potassium hydroxide at reduced pressure overnight. The thus-obtained $N^G$-benzyloxycarbonyl-L-arginine lactam hydrochloride is dissolved in 10 ml of pyridine, cooled to –15° C., then at this temperature a solution of 3.7 g (10 mmole) of O-tetrahydropyranyl-3-cyclohexyl-D-lactyl-L-pipecolic acid (Example 9, Step A) in 10 ml of pyridine, 0.964 ml (10 mmole) of phosphorus oxychloride and 1.85 ml (13.2 mmole) of triethylamine are added. The reaction mixture is stirred for 30 minutes at –15° C. and for one hour at 0° C., then it is evaporated from a water bath at a temperature of about 40° C. at 20–25 millibar. The residue is dissolved in 30 ml of water and 30 ml of ethyl acetate, the ethyl acetate layer is washed with 10 ml portions each of water, 5% sodium hydrogen carbonate solution, water, 1M potassium hydrogen sulfate solution and again water, dried over sodium sulfate, then evaporated from a water bath at about 40° C. at 20–25 millibar. The oily product is submitted to chromatography on a silicagel adsorbent in a developing system of ethyl acetate:pyridine:acetic acid:water (960:20:6:11). The fractions containing the pure product are pooled, extracted with 2×10 ml of 1M potassium hydrogen sulfate solution, washed with water to neutrality and evaporated to dryness at reduced pressure as mentioned above.

Yield: 2.56 g (40%) oil
$R_f(2)$=0.83–0.90

Step 2: O-Tetrahydropyranyl-3-cyclohexyl-D-lactyl-L-pipecolyl-$N^G$-benzyloxycarbonyl-L-arginine aldehyde 2.25 g (3.5 mmole) of O-tetrahydropyranyl-3-cyclohexyl-D-lactyl-L-pipecolyl-$N^G$-benzyloxycarbonyl-L-arginine lactam (Example 9, Step 1) is transformed according to the process described in Example 7, Step 2, applying identical amounts of solvents and reagents.

Yield: 1.46 g (65%)
$R_f(2)$=0.46–0.58
Analysis for $C_{34}H_{51}N_5O_7$ (641.79) Calculated: C %=63.62; H %=8.01; N %=10.91; Found: C %=63.80; H %=8.15; N %=10.9.

Step 3: 3-Cyclohexyl-D-lactyl-L-pipecolyl-L-arginine aldehyde hemisulfate 1.3 g (2 mmole) of O-tetrahydropyranyl-3-cyclohexyl-D-lactyl-L-pipecolyl-$N^G$-benzyloxycarbonyl-L-arginine aldehyde (Example 9, Step 2) is transformed according to the process described in Example 7, Step 3, applying identical amounts of solvents and reagents.

Yield: 0.6 g (60%)

$R_f(5)$=0.51–0.60
HPLC(I/3): k'=7.34, 7.97, 8.18, 8.45, 8.55, 8.90
The FAB mass spectrum confirms the assumed structure (424 [M+H]$^+$).

The starting materials can be prepared as follows:
Step A: O-Tetrahydropyranyl-3-cyclohexyl-D-lactyl-L-pipecolic acid 4.45 g (12.5 mmole) of O-tetrahydropyranyl-3-cyclohexyl-D-lactic acid cyclohexylammonium salt (Example 7, Step C) is dissolved in 15 ml of 1M potassium hydrogen sulfate and 25 ml of methylene chloride. The methylene chloride layer is washed with water, dried over sodium sulfate and evaporated from a water bath at about 40° C. and 20–25 millibar. The resulting O-tetrahydropyranyl-3-cyclohexyl-D-lactic acid is dissolved in 15 ml of dimethyl formamide, cooled in an ice bath, then 2.24 g (12.5 mmole) of L-pipecolic acid methyl ester hydrochloride, 2.10 g (13.75 mmole) of 1-hydroxybenzotriazole hydrate, 1.75 ml (12.5 mmole) of triethylamine and 2.58 g (12.5 mmole) of dicyclohexylcarbodiimide are added. The reaction mixture is left to stand at room temperature overnight, the precipitated dicyclohexylurea is filtered off and the solution is evaporated from a water bath of about 4.0C at 20–25 millibar. The residue is dissolved in 30 ml of methylene chloride, washed with 10 ml each of water, 2×10 ml of 5% sodium hydrogen carbonate and again with water, dried over sodium sulfate, then evaporated from a water bath of about 40° C. at 20–25 millibar. The oily residue [O-tetrahydropyranyl-3-cyclohexyl-D-lactyl-L-pipecolic acid methyl ester; $R_f(9)$= 0.95–0.98] is dissolved in 40 ml of methanol, then 13 ml of 1M sodium hydroxide solution is added and the solution is stirred for 24 hours. Thereafter 15 ml of 1M sodium hydroxide solution and 20 ml of methylene chloride are added. The two layers obtained are separated, the pH of the aqueous layer is adjusted to 3 with 1M potassium hydrogen sulfate under stirring and ice cooling, then extracted with 2×15 ml of methylene chloride. The methylene chloride solutions are pooled, washed to neutrality with water, dried over sodium sulfate and evaporated as described above, yielding 3.75 g (82%) of O-tetrahydropyranyl-3-cyclohexyl-D-lactyl-L-pipecolic acid in amorphous form.

$R_f(9)$=0.51–0.63
Analysis for $C_{20}H_{33}NO_5$ (367.47) Calculated: C %=65.36; H %=9.05; N %=3.81 Found: C %=63.35; H %=9.2; N %=4.0

EXAMPLE 10

D-2-Cyclohexyl-2-hydroxyacetyl-L-pipecolyl-L-arginine aldehyde hemisulfate

Step 1: O-Tetrahydropyranyl-D-2-cyclohexyl-2-hydroxyacetyl-L-pipecolyl-$N^G$-benzyloxycarbonyl-L-arginine lactam Starting from 3.55 g (10 mmole) of O-tetrahydropyranyl-D-2-cyclohexyl-2-hydroxyacetyl-L-pipecolic acid (Example 10, Step A) and 3.9 g (10 mmole) of t-butyloxycarbonyl-$N^G$-benzyloxycarbonyl-L-arginine lactam [S. Bajusz et al.: J. Med. Chem. 33, 1729 (1990)] and proceeding according to the process described in Example 9, Step 1, applying identical amounts of solvents and reagents, 2.8 g (45%) of the aimed product is obtained.

$R_f(2)$=0.80–0.88

Step 2: O-Tetrahydropyranyl-D-2-cyclohexyl-$^2$-hydroxyacetyl-L-pipecolyl-$N^G$-benzyloxycarbonyl-L-arginine aldehyde 2.2 g (3.5 mmole) of O-tetrahydropyranyl-D-2-cyclohexyl-2-hydroxyacetyl-L-pipecolyl-$N^G$- benzyloxycarbonyl-L-arginine lactam (Example 10, Step 1) is transformed according to the process described in Example 9, Step 2, applying identical amounts of solvents and reagents.

Yield 1.45 g (66%)
$R_f(2)=0.42–0.53$

Analysis for $C_{33}H_{49}N_5O_7$ (627.76) Calculated: C %=63.13; H %=7.87; N %=11.16; Found: C %=63.3; H %=7.95; N %=11.0.

Step 3: D-2-Cyclohexyl-2-hydroxyacetyl-L-pipecolyl-L-arginine aldehyde hemisulfate 1.26 g (2 mmole) of O-tetrahydropyranyl-D-2-cyclohexyl-2-hydroxyacetyl-L-pipecolyl-$N^G$-benzyloxycarbonyl-L-arginine aldehyde (Example 10, Step 2) is transformed according to the process described in Example 7, Step 3, applying identical amounts of solvents and reagents.

Yield 0.62 g (65%)
$R_f(5)=0.50–0.58$
HPLC(I/3): k'=6.16, 7.17 and 7.67.

The FAB mass spectrum confirms the assumed structure (410 [M+H]$^+$).

The starting material can be prepared as follows:
Step A: O-Tetrahydropyranyl-D-2-cyclohexyl-2-hydroxyacetyl-L-pipecolic acid Starting from 4.27 g (12.5 mmole) of O-tetrahydropyranyl-D-2-cyclohexyl-2-hydroxyacetic acid cyclohexylammonium salt (Example 8, Step B) and 2.47 g (13.75 mmole) of L-pipecolic acid methyl ester hydrochloride, and proceeding according to the process described in Example 9, Step A, applying identical amounts of solvents and reagents, 3.7 g (84%) of the aimed product is obtained in amorphous form.

$R_f(9)=0.50–0.60$

Analysis for $C_{19}H_{31}NO_5$ (353.45) Calculated: C %=64.56; H %=8.84; N %=3.96; Found: C %=66.65; H %=8.85; N %=4.05.

EXAMPLE 11

D-2-Phenyl-2-hydroxyacetyl-L-pipecolyl-L-arginine aldehyde hemisulfate

Step 1: O-Tetrahydropyranyl-D-2-phenyl-2-hydroxyacetyl-L-pipecolyl-$N^G$-benzyloxycarbonyl-L-arginine lactam Starting from 3.47 g (10 mmole) of O-tetrahydropyranyl-D-2-phenyl-2-hydroxyacetyl-L-pipecolic acid (Example 11, Step A) and 3.9 g (10 mmole) of t-butyloxycarbonyl-$N^G$-benzyloxycarbonyl-L-arginine lactam [S. Bajusz et al.: J. Med. Chem. 33, 1729 (1990)] and proceeding according to the process described in Example 9, Step 1, applying identical amounts of solvents and reagents, 2.54 g (41%) of the aimed product is obtained.

$R_f(2)=0.80–0.85$

Step 2: O-Tetrahydropyranyl-D-2-phenyl-2-hydroxyacetyl-L-pipecolyl-$N^G$-benzyloxycarbonyl-L-arginine aldehyde 2.2 g (3.5 mmole) of O-tetrahydropyranyl-D-2-phenyl-2-hydroxyacetyl-L-pipecolyl-$N^G$-benzyloxycarbonyl-L-arginine lactam (Example 11, Step 1) is transformed according to the process described in Example 9, Step 2, applying identical amounts of solvents and reagents.

Yield 1.3 g (65%)
$R_f(2)=0.40–0.45$

Step 3: D-2-Phenyl-2-hydroxyacetyl-L-pipecolyl-L-arginine aldehyde hemisulfate 1.24 g (2 mmole) of O-tetrahydropyranyl-D-2-phenyl-2-hydroxyacetyl-L-pipecolyl-$N^G$-benzyloxycarbonyl-L-arginine aldehyde (Example 11, Step 2) is transformed according to the process described in Example 7, Step 3, applying identical amounts of solvents and reagents.

Yield 0.56 g (60%)
$R_f(5)=0.48–0.53$
HPLC(I/2): k'=4.55, 5.78 and 10.78.

The FAB mass spectrum confirms the assumed structure (404 [M+H]$^+$).

The starting material can be prepared as follows:
Step A: O-Tetrahydropyranyl-D-2-phenyl-2-hydroxyacetyl-L-pipecolic acid Starting from 4.2 g (12.5 mmole) of O-tetrahydropyranyl-D-2-phenyl-2-hydroxyacetyl cyclohexylammonium salt (Example 6, Step A) and 2.47 g (13.75 mmole) of L-pipecolic acid methyl ester hydrochloride and proceeding according to the process described in Example 9, Step A, applying identical amounts of solvents and reagents, 3.65 g (84%) of the aimed product is obtained in amorphous form.

$R_f(9)=0.43–0.53$

Analysis for $C_{19}H_{25}NO_5$ (347.40) Calculated: C %=65.69; H %=7.25; N %=4.03; Found: C %=65.8; H %=7.4; N %=4.3.

EXAMPLE 12

3,3-Diphenyl-D-lactyl-L-prolyl-L-arginine aldehyde hemisulfate

Step 1: O-Tetrahydropyranyl-3,3-diphenyl-D-lactyl-L-prolyl-$N^G$-benzyloxycarbonyl-L-arginine lactam 2.73 g (7 mmole) of t-butyloxycarbonyl-$N^G$-benzyloxycarbonyl-L-arginine lactam [S. Bajusz et al.: J. Med. Chem. 33, 1729 (1990)] is suspended in 10 ml of chloroform, then 10 ml of ethyl acetate containing hydrogen chloride gas (concentration: 0.11–0.15 g/ml) is added under stirring and cooling in ice water. After two hours the reaction mixture is diluted with 10–15 ml of diethyl ether, the crystals formed are filtered, washed with 5 ml of acetone and 5 ml of diethyl ether and dried over potassium hydroxide at reduced pressure overnight. The $N^G$-benzyloxycarbonyl-L-arginine lactam hydrochloride obtained is dissolved in 10 ml of dimethyl formamide, cooled to –20° C. and added to the mixed anhydride to be prepared as follows:

2.60 g (6 mmole) of O-tetrahydropyranyl-3,3-diphenyl-DL-lactyl-L-proline hemihydrate (Example 12, Step E) is dissolved in 6 ml of dimethyl formamide, refrigerated to –20° C., then under stirring 0.66 ml (6 mmole) of N-methylmorpholine and 0.79 ml of isobutyl chloroformate are added. Stirring is continued for 10 minutes, then the above suspension of $N^G$-benzyloxycarbonyl-L-arginine lactam in dimethyl formamide and finally 2.1 ml (15 mmole) of triethylamine are added. Stirring is continued for 2 hours under cooling, then the mixture is left to warm up to room temperature. Thereafter the salts are filtered off and the filtrate is diluted with 40 ml of methylene chloride. The solution obtained is washed with 10 ml of 1M potassium hydrogen sulfate, 3×10 ml of water, dried over sodium sulfate and evaporated from a water bath at about 30° C. at 20–25 millibar. The resulting 3.8 g (90%) of the product—a mixture of compounds containing 3,3-diphenyl-D and L-lactic acid residues—is submitted to chromatography on a silicagel column, applying a mixture of ethyl acetate and diisopropyl ether (7:3) as developing solvent ($R_f$=0.23–0.27 and 0.28–0.32 in this system). The fractions containing the pure D product, migrating with higher $R_f$ value, and those containing the pure L product, migrating with lower $R_f$ value, are combined, evaporated from a water bath at about 30° C. and 20–25 millibar and finally worked up with diisopropyl ether. Yield 1.0 g (48%) of D and 0.98 g (47%) of L product. Product D is the peptide lactam containing 3,3-diphenyl-D-lactic acid residue. The aldehyde derivative with high antithrombin activity is prepared from this product by the process described in Steps 2 and 3 of this Example.

$R_f(10)$=0.28–0.32

M.p.: 156° C. (sintering at 150° C.)

Analysis for $C_{39}H_{45}N_5O_7$ (695.79) Calculated: C %=67.32; H %=6.52; N %=10.07; Found: C %=67.4; H %=6.65; N %=10.0.

Step 2: O-Tetrahydropyranyl-3,3-diphenyl-D-lactyl-L-prolyl-$N^G$-benzyloxycarbonyl-L-arginine aldehyde 0.95 g (1.36 mmole) of O-tetrahydropyranyl-3,3-diphenyl-D-lactyl-L-prolyl-$N^G$-benzyloxycarbonyl-L-arginine lactam (Example 12, Step 1) is dissolved in 8 ml of tetrahydrofuran, then under stirring and at a temperature below −20° C. 1.02 mmole of lithium aluminium hydride—dissolved in tetrahydrofuran—is added. The progress of the reduction is monitored by thin-layer chromatography, applying ethyl acetate:pyridine:acetic acid:water (240:20:6:11) as developing system. If required, further portions of lithium aluminium hydride are added, then cool 0.5M sulfuric acid is added dropwise to the reaction mixture under cooling and stirring, adjusting the pH to 3. The solution obtained is extracted with 5 ml of diethyl ether. To the bottom layer 5% sodium hydrogen carbonate solution is added, adjusting the pH to about 6.5, then the solution is extracted with 3×5 ml of methylene chloride. The methylene chloride solutions are pooled, dried over sodium sulfate and evaporated from a water bath at about 40° C. at 20–25 millibar. The residue is worked up with diisopropyl ether, filtered and dried at reduced pressure.

Yield 0.86 g (90%)

$R_f(2)$=0.38–0.42

Step 3: 3,3-Diphenyl-D-lactyl-L-prolyl-L-arginine aldehyde hemisulfate 0.8 g (1.15 mmole) of O-tetrahydropyranyl-3,3-diphenyl-D-lactyl-L-prolyl-$N^G$-benzyloxycarbonyl-L-arginine aldehyde (Example 12, Step 2) [$R_f(4)$=0.80–0.85] is dissolved in a mixture of 6 ml of dimethyl formamide and 1.2 ml of 0.5M sulfuric acid, 0.12 g of Pd—C catalyst is added and the mixture is submitted to hydrogenation at about 10° C. The progress of the reaction is monitored by thin-layer chromatography. The intermediary product—devoid of benzyloxycarbonyl group—has $R_f(4)$=0.43–0.47. The reaction is completed in about 30 minutes, the catalyst is filtered off, washed with 1 ml of 50% aqueous dimethyl formamide and 1 ml of water, then the combined solutions are evaporated from a water bath at about 40° C. and 20–25 millibar. The oily residue is dissolved in 10 ml of water, the pH of the solution is adjusted to 2.8 with sulfuric acid or an anion-exchange resin (HO⁻) and the solution is left to stand at room temperature for about 24 hours up to the full deblocking of the O-tetrahydropyranyl protecting group [$R_f(4)$= 0.40–0.50]. The aqueous solution is washed with 3×5 ml of methylene chloride, the pH is adjusted with an anion-exchange resin (HO⁻) to 3.6, then the solution is frozen and freeze-dried.

Yield 0.5 g (70%)

$R_f(5)$=0.48–0.52

HPLC(I/3): k'=7.8 and 8.23

The FAB mass spectrum confirms the assumed structure (480 [M+H]⁺).

The starting materials can be prepared as follows:

O-Tetrahydropyranyl-3,3-diphenyl-DL-lactyl-L-proline

Step A: 3,3-Diphenyl-DL-lactic acid methyl ester 22.33 g (0.1 mole) of 3,3-diphenyl-DL-lactic acid nitrile [Wiese: Ann. 248, 39–41 (1888)] is dissolved in 100 ml of diethyl ether, and then 4.04 ml (0.1 mole) of methanol is added. The solution is saturated with dry hydrogen chloride gas under ice cooling, then it is left to stand for one hour and evaporated from a water bath at about 40° C. at 20–25 millibar. The residue is crystallized with about 200 ml of diethyl ether, the crystals are filtered off, washed with diethyl ether and dried at reduced pressure. The product obtained [20.55 g (70%), 3,3-diphenyl-DL-lactiminomethyl ether hydrochloride, (m.p.: 82°–83° C.)] is suspended in 140 ml of water and heated to 50°–60° C. for 1–2 hours. An oily product is formed which solidifies under cooling and stirring. The solid product is filtered, washed with water and then with n-hexane and finally dried at reduced pressure.

Yield 12.8 g (50%) (calculated for the nitrile).

$R_f(12)$=0.4; m.p.: 49°–50° C.

Analysis for $C_{16}H_{16}O_3$ (256.29) Calculated: C %=74.98; H %=6.29 Found: C %=75.0; H %=6.3.

Step B: O-Tetrahydropyranyl-3,3-diphenyl-DL-lactic acid methyl ester 7.83 g (30.5 mmole) of 3,3-diphenyl-DL-lactic acid methyl ester (Example 12, Step A) is dissolved in 75 ml of methylene chloride, then under stirring and ice cooling 3.83 ml of dihydropyran (40 mmole) and 0.8 ml of ethyl acetate, containing hydrogen chloride gas (concentration: 0.11–0.15 g/ml) are added. The solution is left to stand overnight, then it is diluted with 50 ml of methylene chloride, washed to neutrality with water, dried over calcium chloride and evaporated from a water bath at about 30° C. and 20–25 millibar. The residue is 30.5 mmole of O-tetrahydropyranyl-3,3-diphenyl-DL-lactic acid methyl ester and is used in this form in Step C.

Step C: O-Tetrahydropyranyl-3,3-diphenyl-DL-lactic acid hydrate 30.5 mmole of O-tetrahydropyranyl-3,3-diphenyl-DL-lactic acid methyl ester (Example 12, Step B) is dissolved in 30.5 ml of acetone and 30.5 ml of ethanol containing 1M of potassium hydroxide. The progress of the reaction is monitored by thin-layer chromatography. The solution is evaporated from a water bath at about 40° C. and 20–25 millibar. The residue is dissolved in 40 ml of water, washed with 2×10 ml of diethyl ether, then acidified to pH 3 with 1M potassium hydrogen sulfate under ice cooling. The separating solid product is filtered off, washed with water and dried at reduced pressure.

Yield 7.9 g (75%); m.p.: 115°–117° C. (sintering at 76° C.)

$R_f(9)$=0.65–0.75

Analysis for $C_{20}H_{22}O_4 \cdot H_2O$ (344.39) Calculated: C %=69.75; H %=7.02; Found: C %=69.7; H %=6.55.

Step D: O-Tetrahydropyranyl-3,3-diphenyl-DL-lactic acid 2,4,5-trichlorophenyl ester 4.5 g (13 mmole) of O-tetrahydropyranyl-3,3-diphenyl-DL-lactic acid hydrate (Example 12, Step C) and 2.8 g (14.2 mmole) of 2,4,5-trichlorophenol are dissolved in 15 ml of tetrahydrofuran, then under stirring and ice cooling 2.8 g (13.6 mmole) of dicyclohexylcarbodiimide is added. The reaction mixture is left to stand at room temperature for 3 hours, the precipitated dicyclohexylurea is filtered off and washed with tetrahydrofuran. The tetrahydrofuran solutions are combined and evaporated from a water bath at about 40° C. and 20–25 millibar. The residue is worked up with 15 ml of diisopropyl ether. The suspension is cooled with ice water, 5 ml of n-hexan is added, then the suspension is filtered. The solid product is washed with a mixture of diisopropyl ether and n-hexane (1:1) and dried at reduced pressure. The product obtained is O-tetrahydropyranyl-3,3-diphenyl-DL-lactic acid 2,4,5-trichlorophenyl ester [4.6 g (10 mmole), $R_f(11)$=0.75–0.85].

Step E: O-Tetrahydropyranyl-3,3-diphenyl-DL-lactyl-L-proline hemihydrate 10 mmole of O-tetrahydropyranyl-3,3-diphenyl-DL-lactic acid 2,4,5-trichlorophenyl ester (Example 12, Step D) is dissolved in 10 ml of pyridine, then 1.15 g (10 mmole) of L-proline and 1.4 ml (10 mmole) of triethylamine are added. The reaction mixture is stirred at room temperature for 6 hours, then evaporated from a water bath at about 40° C. and 20–25 millibar. The residue is dissolved in 20 ml of water and 10 ml of diethyl ether. The aqueous layer is washed with 10 ml of diethyl ether, acidified with 1M potassium hydrogen sulfate to pH 3 under ice cooling and extracted with 3×10 ml of diethyl ether. The combined diethyl ether solutions are washed with water, dried over sodium sulfate and evaporated as described above. The residue is worked up with 10 ml of diisopropyl ether, the suspension is cooled with ice water, then filtered, washed with cold diisopropyl ether and dried at reduced pressure.

Yield 3.05 g (70%)

$R_f(2)$=0.45–0.55; m.p.: 132°–135° C.

Analysis for $C_{25}H_{29}NO_5 \cdot \frac{1}{2}H_2O$ (432.50) Calculated: C %=69.42; H %=6.99; N %=3.24; Found: C %=69.4; H %=6.85; N %=3.2.

EXAMPLE 13

D-2-(2-Naphthyl)-2-hydroxyacetyl-L-prolyl-L-arginine aldehyde hemisulfate

Step 1: O-t-Butyl-D-2-(2-naphthyl)-2-hydroxyacetyl-L-prolyl-$N^G$-benzyloxycarbonyl-L-arginine lactam 3.12 g (8 mmole) of t-butyloxycarbonyl-$N^G$-benzyloxycarbonyl-L-arginine lactam [S. Bajusz et al.: J. Med. Chem. 33, 1729 (1990)] is suspended in 12 ml of chloroform, then under stirring and ice cooling 12 ml of ethyl acetate containing hydrogen chloride gas (concentration: 0.11–0.15 g/ml) is added. After two hours the reaction mixture is diluted with 15 ml of diethyl ether, the precipitated crystalline product is filtered off, washed with 6 ml of acetone and 6 ml of diethyl ether and dried over potassium hydroxide under reduced pressure overnight. The obtained $N^G$-benzyloxycarbonyl-L-arginine lactam hydrochloride is dissolved in 12 ml of dimethyl formamide, refrigerated to −20° C. and added to the mixed anhydride to be prepared as follows: 2.8 g (7.8 mmole) of O-t-butyl-D-2-(2-naphthyl)-2-hydroxyacetyl-L-proline (Example 13, Step F) is dissolved in 8 ml of dimethyl formamide, then under stirring and at −20° C. 0.87 ml (7.8 mmole) of N-methylmorpholine, 1.03 ml of isobutyl chloroformate, then after 10 minutes the above suspension of $N^G$-benzyloxycarbonyl-L-arginine lactam in dimethyl formamide, finally 2.8 ml (20 mmole) of triethylamine are added. The reaction mixture is stirred under cooling for 2 hours, then left to warm up to room temperature. Thereafter the salts are filtered off and the filtrate is diluted with 50 ml of benzene. The solution obtained is washed with 15 ml of 1M potassium hydrogen sulfate solution and 3×15 ml of water, dried over sodium sulfate and evaporated from a water bath at about 40° C. and 20–25 millibar. The residue is worked up with n-hexane, filtered, washed with n-hexane and dried at reduced pressure.

Yield 4.14 g (85%)

$R_f(9)$=0.72–0.75

Step 2: D-2-(2-Naphthyl)-2-hydroxyacetyl-L-prolyl-$N^G$-benzyloxycarbonyl-L-arginine lactam 4.08 g (6.5 mmole) of O-t-butyl-D-2-(2-naphthyl)-2-hydroxyacetyl-L-prolyl-$N^G$-benzyloxycarbonyl-L-arginine lactam (Example 13, Step 1) is dissolved in 20 ml of a mixture of trifluoroacetic acid and methylene chloride (1:1) and left to stand at room temperature for 30 minutes. The reaction mixture is diluted with 40 ml of methylene chloride, washed to neutrality with 3×20 ml of water and 20 ml of 5% sodium hydrogen carbonate, dried over sodium sulfate and evaporated from a water bath at about 40° C. and 20–25 millibar. The residue is submitted to chromatography on a column prepared from 100 g of silicagel in a developing system of ethyl acetate: pyridine:acetic acid:water (480:20:6:11). The fractions containing the pure product migrating with $R_f(7)$=0.44–0.46 are pooled, washed with 1M potassium hydrogen sulfate solution and water, dried over sodium sulfate and evaporated from a water bath at about 40° C. and 20–25 millibar. The residue is worked up with n-hexane, filtered, washed with n-hexane and dried at reduced pressure.

Yield 1.8 g (48%)

$R_f(7)$=0.44–0.46

Analysis for $C_{31}H_{33}N_5O_6$ (571.14) Calculated: C %=65.12; H %=5.82; N %=12.25; Found: C %=65.2; H %=5.9; N %=12.2.

Step 3: D-2-(2-Naphthyl)-2-hydroxyacetyl-L-prolyl-$N^G$-benzyloxycarbonyl-L-arginine aldehyde 1.71 g (3 mmole) of D-2-(2-naphthyl)-2-hydroxyacetyl-L-prolyl-$N^G$-benzyloxycarbonyl-L-arginine lactam (Example 13, Step 2) is dissolved in 15 ml of tetrahydrofuran, then under stirring and at a temperature not exceeding −20° C. a solution of 2.25 mmole of lithium aluminium hydride in tetrahydrofuran is added. The progress of the reaction is monitored by thin-layer chromatography in a solvent system of ethyl acetate:pyridine:acetic acid:water (30:20:6:11) and, if required, further portions of lithium aluminium hydride are added. Thereafter cool 0.5M sulfuric acid is added under stirring and cooling to ensure a pH value of 3–4 in the reaction mixture. The resulting solution is diluted with 15 ml of water, washed with 10 ml of ethyl acetate and extracted with 3×10 ml of n-butanol saturated with water. The n-butanol solutions are combined, washed with 10 ml of 5% sodium hydrogen carbonate solution and 2×10 ml of water saturated with n-butanol, then evaporated from a water bath at about 40° C. and 20–25 millibar. The residue is worked up with n-hexane, filtered, washed with n-hexane and dried at reduced pressure.

Yield 1.13 g (65.7%)

$R_f(6)$=0.62–0.66

Step 4: D-2-(2-Naphthyl)-2-hydroxyacetyl-L-prolyl-L-arginine aldehyde hemisulfate 1.0 g (1.75 mmole) of D-2-(2-naphthyl)-2-hydroxyacetyl-L-prolyl-$N^G$-benzyloxycarbonyl-L-arginine aldehyde (Example 13, Step 3) is dissolved in 20 ml of ethanol, 1.75 ml of 0.5M sulfuric acid and 2 ml of water are added and the solution is submitted to hydrogenation in the presence of Pd—C catalyst. The reaction is monitored by thin-layer chromatography in the solvent system ethyl acetate:pyridine:acetic acid:water (30:20:6:11). The reaction is completed within about 4 hours, then the catalyst is filtered off, washed with 5 ml of 60% aqueous ethanol and 5 ml of water. The ethanol is distilled off from the filtrate under reduced pressure, then 15 ml of water is added, the solution is washed with 10 ml of methylene chloride and its pH is adjusted to 3.3 with sulfuric acid or anion-exchange resin (HO−). If the solution obtained is not entirely clear (cloudy due to precipitated material), the precipitated material is dissolved by adding 0.5–1.5 ml of t-butanol (max. 10%), the clear solution is frozen and freeze-dried.

Yield 0.78 g (88%)

$R_f(5)$=0.29–0.32

HPLC(I/1): k'=8.25, 9.25 and 11.3.

The FAB mass spectrum confirms the assumed structure (440 [M+H]$^+$).

The starting material can be prepared as follows:

O-t-Butyl-D-2-(2-naphthyl)-2-hydroxyacetyl-L-proline

Step A: DL-2-(2-naphthyl)-2-hydroxyacetic acid methyl ester

Starting from 20.2 g (100 mmole) of DL-2-(2-naphthyl)-2-hydroxyacetic acid [I. M. Panaiotov: Compt. rend. acad. bulgare sci. 10, No. 2, 137–140 (1957); Chem. Abstr. 52, 5336e (1958); m.p.: 158°–160° C.; $R_f(8)=0.28$–0.30] and proceeding according to the process described in Example 7, Step B, applying identical amounts of solvents and reagents, 22 g of an oily product is obtained [$R_f(2)=0.79$–0.81] which is considered 100 mmole of DL-2-(2-naphthyl)-2-hydroxyacetic acid methyl ester.

Step B: O-t-Butyl-DL-2-(2-naphthyl)-2-hydroxyacetic acid methyl ester 100 mmole of DL-2-(2-naphthyl)-2-hydroxyacetic acid methyl ester (Example 13, Step A) is dissolved in 100 ml of methylene chloride. The solution is cooled to −25° C., 0.88 ml (10 mmole) of trifluoromethanesulfonic acid and 116–120 ml of isobutylene are added and the mixture is left to stand at −20° C. for 30 minutes. Then 1.0 ml of pyridine is added and the reaction mixture is left to warm up to room temperature, then it is evaporated from a water bath at about 40° C. and 20–25 millibar. The evaporation residue is dissolved in 100 ml of benzene, washed with 20 ml portions of water, 5% sodium hydrogen carbonate solution, water, 1M potassium hydrogen sulfate and again with water, then dried over sodium sulfate and evaporated from a water bath at about 40° C. and 20–25 millibar. The residue is considered 100 mmole of O-t-butyl-DL-2-(2-naphthyl)-2-hydroxyacetic acid methyl ester and used in Step C [$R_f(12)=0.50$–0.55].

Step C: O-t-Butyl-DL-2-(2-naphthyl)-2-hydroxyacetic acid 100 mmole of O-t-butyl-DL-2-(2-naphthyl)-2-hydroxyacetic acid methyl ester (Example 13, Step B) is dissolved in 100 ml of methanol, 50 ml of 2M sodium hydroxide solution is added and the solution is stirred at room temperature overnight. The reaction mixture is saturated with carbon dioxide by adding dry-ice, washed with 2×20 ml of n-hexane, acidified with solid potassium hydrogen sulfate and extracted with 3×40 ml of ethyl acetate. The ethyl acetate layers are combined, washed to neutrality with water, dried over sodium sulfate and evaporated from a water bath at about 40° C. and 20–25 millibar. The oily residue is mixed with 100 ml of n-hexane, the crystals formed are filtered, washed with n-hexane and dried at reduced pressure.

Yield 13.2 g (51%); m.p.: 114°–116° C.

$R_f(9)=0.34$–0.38

Analysis for $C_{16}H_{18}O_3$ (258.30) Calculated: C %=74.39; H %=7.02; Found: C %=74.0; H %=7.0

Step D: O-t-Butyl-DL-2-(2-naphthyl)-2-hydroxyacetic acid 2,4,5-trichlorophenyl ester 12.9 g (50 mmole) of O-t-butyl-DL-2-(2-naphthyl)-2-hydroxyacetic acid (Example 13, Step C) and 10.24 g (52 mmole) of 2,4,5-trichlorophenol are dissolved in 30 ml of dimethyl formamide and cooled to 0° C. 10.3 g (50 mmole) of dicyclohexylcarbodiimide is added and the mixture is stirred at room temperature for 2 hours. The precipitated dicyclohexylurea is filtered off and washed with 2×5 ml of dimethyl formamide, then the filtrate and the washings are combined. The solution obtained is considered 50 mmole of O-t-butyl-DL-2-(2-naphthyl)-2-hydroxyacetic acid 2,4,5-trichlorophenyl ester [$R_f(9)=0.82$–0.85] used in the next reaction step as a solution in dimethyl formamide.

Step E: O-t-Butyl-DL-2-(2-naphthyl)-2-hydroxyacetyl-L-proline

To the dimethyl formamide solution of O-t-butyl-DL-2-(2-naphthyl)-2-hydroxyacetic acid 2,4,5-trichlorophenyl ester (50 mmole), obtained in Example 13, Step D, 5.8 g (50 mmole) of L-proline and 7.0 ml (50 mmole) of triethylamine are added, then the mixture is stirred at room temperature for 24 hours. The reaction mixture is filtered and evaporated from a water bath at about 40° C. and 20–25 millibar. Thereafter 60 ml of 5% sodium hydrogen carbonate is added to the oily residue. The cloudy solution is washed with 3×40 ml of diethyl ether, the pH is adjusted to 3 by adding solid potassium hydrogen sulfate, then the solution is extracted with 3×40 ml of ethyl acetate. The combined ethyl acetate solutions are washed to neutrality with water, dried over sodium sulfate and evaporated from a water bath at about 40° C. and 20–25 millibar. The resulting 18 g oily residue is considered the diastereomer mixture of O-t-butyl-D-2-(2-naphthyl)-2-hydroxyacetyl-L-proline [25 mmole; $R_f(1)=0.38$–0.40] and O-t-butyl-L-2-(2-naphthyl)-2-hydroxyacetyl-L-proline [25 mmole; $R_f(1)=0.35$–0.37] and is used in this oil form in the next step (F).

Step F: O-t-Butyl-D-2-(2-naphthyl)-2-hydroxyacetyl-L-proline 2000 ml of BIO-RAD AG 1-X2 (50–100 mesh) anion-exchange resin (acetate cycle, anion capacity .1200 mequiv.) is suspended in distilled water, poured into a glass column (80×6 cm), then 4000 ml of a mixture of methanol and water (2:1) is run through it at a flow rate of 15 ml/min. Thereafter the solution of 18 g of an oil, prepared in Example 13, Step E, dissolved in 2000 ml of a mixture of methanol and water (2:1), is applied on it, then the resin is washed with 4000 ml of the above mixture of methanol and water. A mixture of methanol and 1M acetic acid (2:1) is used for eluting the product, collecting 200 ml fractions. The fractions are monitored by thin-layer chromatography in the system of ethyl acetate:pyridine:acetic acid:water (480:20:6:11), the spots are visualized under UV light or by developing in $KMnO_4$. The fractions containing the pure isomers are combined and concentrated to a third volume on a water bath at about 40° C. and 20–25 millibar. The precipitated product is redissolved by the addition of acetonitrile and the solutions are frozen and freeze-dried. Yields:

Isomer I [$R_f(1)=0.38$–0.40] 5.93 g

Isomer II [$R_f(1)=0.35$–0.37] 5.63 g.

Mixture of isomers I and II 1.0 g.

On the basis of the chromatographic properties and enzyme inhibitory activities of the aldehyde derivatives prepared from them, isomer I is O-t-butyl-D-2-(2-napthyl)-2-hydroxyacetyl-L-proline [5.93 g (16.68 mmole), 66.7% (calculated for the intermediary product O-t-butyl-DL-2-(2-naphthyl)-2-hydroxyacetic acid, used in Example 13, Step D)], m.p.: 90°–93° C.

Analysis for $C_{21}H_{25}NO_4$ (355.42) Calculated: C %=70.96; H %=7.09; N %=3.94; Found: C %=71.0; H %=7.15; N %=3.85.

EXAMPLE 14

D-2-(1-Naphthyl)-2-hydroxyacetyl-L-prolyl-L-arginine aldehyde hemisulfate

Step 1: O-t-Butyl-D-2-(1-naphthyl)-2-hydroxyacetyl-L-prolyl-$N^G$-benzyloxycarbonyl-L-arginine lactam Starting from 3.12 g (8 mmole) of t-butyloxycarbonyl-$N^G$-benzyloxycarbonyl-L-arginine lactam [S. Bajusz et al.: J. Med. Chem. 33, 1729 (1990)] and 2.8 g (7.8 mmole) of O-t-butyl-D-2-(1-naphthyl)-2-hydroxyacetyl-L-proline (Example 14, Step F) and proceeding according to the process described in Example 13, Step 1, applying identical amounts of solvents and reagents, 4.14 g (85%) of the product is obtained.

$R_f(9)=0.71$–0.77

Step 2: D-2-(1-Naphthyl)-2-hydroxyacetyl-L-prolyl-$N^G$-benzyloxycarbonyl-L-arginine lactam Transforming 4.08 g (6.5 mmole) of O-t-butyl-D-2-(1-naphthyl)-2-hydroxyacetyl-L-prolyl-$N^G$-benzyloxycarbonyl-L-arginine lactam (Example 14, Step 1) according to the process described in Example 13, Step 2, applying identical amounts of solvents and reagents, 1.85 g (50%) of the product is obtained.

$R_f(9)$=0.44–0.46.

Analysis for $C_{31}H_{33}N_5O_6$ (571.61) Calculated: C %=65.13; H %=5.82; N %=12.25; Found: C %=65.0 H %=5.95 N %=12.0.

Step 3: D-2-(1-Naphthyl)-2-hydroxyacetyl-L-prolyl-$N^G$-benzyloxycarbonyl-L-arginine aldehyde Transforming 1.71 g (3 mmole) of D-2-(1-naphthyl)-2-hydroxyacetyl-L-prolyl-$N^G$-benzyloxycarbonyl-L-arginine lactam (Example 14, Step 2) according to the process described in Example 13, Step 3, applying identical amounts of solvents and reagents, 1.2 g (70%) of the product is obtained.

$R_f(3)$=0.40–0.44

Step 4: D-2-(1-Naphthyl)-2-hydroxyacetyl-L-prolyl-L-arginine aldehyde hemisulfate Transforming 1.0 g (1.75 mmole) of D-2-(1-naphthyl)-2-hydroxyacetyl-L-prolyl-$N^G$-benzyloxycarbonyl-L-arginine aldehyde (Example 14, Step 3) according to the process described in Example 13, Step 4, applying identical amounts of solvents and reagents, 0.8 g (90%) of the product is obtained.

$R_f(5)$=0.28–0.30

HPLC(I/3): k'=5.99, 6.39 and 7.17.

The FAB mass spectrum confirms the assumed structure (440 [M+H]$^+$).

The starting materials can be prepared as follows:

O-t-Butyl-D-2-(-naphthyl)-2-hydroxyacetyl-L-proline

Step A: DL-2-(1-naphthyl)-2-hydroxyacetic acid methyl ester

Starting from 20.2.g (100 mmole) of DL-2-(1-naphthyl)-2-hydroxyacetic acid [I. M. Panaiotov: Compt rend. acad. bulgare sci. 10, No. 2, 137–140 (1957); Chem. Abstr. 52, 5336e (1958); m.p.: 92°–94° C.; $R_f(2)$=0.28–0.30] and proceeding according to the process described in Example 7, Step B, applying proportional amounts of solvents and reagents, an oily product [$R_f(2)$=0.69–0.71], is obtained which is considered 100 mmole of DL-2-(1-naphthyl)-2-hydroxyacetic acid methyl ester.

Step B: O-t-Butyl-DL-2-(1-naphthyl)-2-hydroxyacetic acid methyl ester

Starting from 100 mmole of DL-2-(1-naphthyl)-2-hydroxyacetic acid methyl ester (Example 14, Step A) and proceeding according to the process described in Example 13, Step B, applying identical amounts of solvents and reagents, 100 mmole of O-t-butyl-DL-2-(1-naphthyl)-2-hydroxyacetic acid methyl ester is obtained and applied in the next step.

$R_f(12)$=0.66–0.70.

Step C: O-t-Butyl-DL-2-(1-naphthyl)-2-hydroxyacetic acid

Starting from 100 mmole of O-t-butyl-DL-2-(1-naphthyl)-2-hydroxyacetic acid methyl ester (Example 14, Step B) and proceeding according to the process described in Example 13, Step C, applying identical amounts, of solvents and reagents, 14.6 g (56.5%) of the product is obtained.

$R_f(9)$=0.73–0.76; m.p.: 132°–135° C.

Analysis for $C_{16}H_{18}O_3$ (258.30) Calculated: C %=74.39; H %=7.02; Found: C %=74.3; H %=7.05.

Step D: O-t-Butyl-DL-2-(1-naphthyl)-2-hydroxyacetic acid 2,4,5-trichlorophenyl ester Starting from 12.9 g (50 mmole) of O-t-butyl-DL-2-(1-naphthyl)-2-hydroxyacetic acid (Example 14, Step C) and 10.24 g (52 mmole) of 2,4,5-trichlorophenol and proceeding according to the process described in Example 13, Step D, applying identical amounts of solvents and reagents, a dimethyl formamide solution is obtained which is considered 50 mmole of O-t-butyl-DL-2-(1-naphthyl)-2-hydroxyacetic acid 2,4,5-trichlorophenyl ester [$R_f(9)$= 0.84–0.86] and is directly applied in the next step.

Step E: O-t-Butyl-DL-2-(1-naphthyl)-2-hydroxyacetyl-L-proline

Starting from 50 mmole of O-t-butyl-DL-2-(1-naphthyl)-2-hydroxyacetic acid 2,4,5-trichlorophenyl ester (Example 14, Step D) and 5.8 g (50 mmole) of L-proline and proceeding according to the process described in Example 13, Step E, applying identical amounts of solvents and reagents, 15.65 g of an oily residue is obtained [$R_f(1)$=0.53–0.55); HPLC(II/5): k'=12.85 and 16.95] which is considered the mixture of 22 mmole of O-t-butyl-D-2-(1-naphthyl)-2-hydroxyacetyl-L-proline and 22 mmole of O-t-butyl-L-2-(1-naphthyl)-2-hydroxyacetyl-L-proline and is used in this oil form in the next (F) step.

Step F: O-t-Butyl-D-2-(1-naphthyl)-2-hydroxyacetyl-L-proline

The 15.65 g of oily product, obtained in Example 14, Step E, is submitted to chromatography according to the method applied in Example 13, Step F on the anion-exchange resin BIO-RAD AG 1-X2 (acetate cycle), except that the content of the fractions is assayed by HPLC under conditions specified in Step E (II/5). The following products are obtained:

Isomer I 4.4 g (k'=12.84) eluted first

Isomer II 4.3 g (k'=16.95) eluted last.

Mixture of isomers I and II 4.5 g.

On the basis of the chromatographic properties and enzyme inhibitory activities of the aldehyde derivatives prepared from them, isomer I is O-t-butyl-D-2-(1-napthyl)-2-hydroxyacetyl-L-proline [4.4 g (12.4 mmole), 49.6 % (calculated for the intermediary product O-t-butyl-DL-2-(1-naphthyl-2-hydroxyacetic acid, used in Example 14, Step D); m.p.: 88°–90° C.].

Analysis for $C_{21}H_{25}NO_4$ (355.42) Calculated: C %=70.96; H %=7.09; N %=3.94; Found: C %=70.95; H %=7.15; N %=3.8.

What we claim is:

1. A peptide derivative selected from the group consisting of

D-isochroman-1-carbonyl-L-prolyl-L-arginine aldehyde,

L-isochroman-1-carbonyl-L-prolyl-L-arginine aldehyde,

D-isochroman-3-carbonyl-L-prolyl-L-arginine aldehyde,

L-isochroman-3-carbonyl-L-prolyl-L-arginine aldehyde,

D-2-phenyl-2-hydroxyacetyl-L-prolyl-L-arginine aldehyde, 2-(9-fluorenyl)-2-hydroxyacetyl-L-prolyl-L-arginine aldehyde, 3-cyclohexyl-D-lactyl-L-prolyl-L-arginine aldehyde, D-2-phenyl-2-hydroxyacetyl-L-pipecolyl-L-arginine aldehyde, D-2-cyclohexyl-2-hydroxyacetyl-L-pipecolyl-L-arginine aldehyde, 3-cyclohexyl-D-lactyl-L-pipecolyl-L-arginine aldehyde, and 3,3-diphenyl-D-lactyl-L-prolyl-L-arginine aldehyde and the acid-addition salts of these compounds.

2. 3-Cyclohexyl-D-lactyl-L-prolyl-L-arginine aldehyde hemisulfate.

3. 3,3-Diphenyl-D-lactyl-L-prolyl-L-arginine aldehyde hemisulfate.

* * * * *